United States Patent [19]
Bonnet et al.

[11] Patent Number: 5,303,702
[45] Date of Patent: Apr. 19, 1994

[54] AUTOMATIC ADJUSTMENT OF THE CONTROL FUNCTION FOR A RATE ADAPTIVE PACEMAKER

[75] Inventors: Jean-Luc Bonnet, Paris; Odile Malherbe, Cachan, both of France

[73] Assignee: ELA Medical, Montrouge, France

[21] Appl. No.: 813,204

[22] Filed: Dec. 23, 1991

[30] Foreign Application Priority Data

Dec. 27, 1990 [FR] France .................. 90 16293

[51] Int. Cl.[5] ............................................. A61N 1/362
[52] U.S. Cl. ..................................................... 607/20
[58] Field of Search .................. 128/419 PG

[56] References Cited

U.S. PATENT DOCUMENTS

| | | | |
|---|---|---|---|
| 4,535,774 | 8/1985 | Olson | 128/419 |
| 4,566,456 | 1/1986 | Koning et al. | 128/419 |
| 4,596,251 | 6/1986 | Plicchi et al. | 128/419 |
| 4,702,253 | 10/1987 | Nappholtz et al. | 128/419 |
| 4,803,987 | 2/1989 | Calfee et al. | 128/419 |
| 4,870,968 | 10/1989 | Wirtzfeld et al. | 128/419 PG |
| 4,901,725 | 2/1990 | Napholtz et al. | 128/419 |
| 4,922,907 | 5/1990 | Hedin et al. | 128/419 P |
| 4,940,052 | 7/1990 | Mann et al. | 128/419 |
| 4,972,834 | 11/1990 | Begemann et al. | 128/419 |

FOREIGN PATENT DOCUMENTS

| | | | |
|---|---|---|---|
| 140472 | 6/1984 | European Pat. Off. | A61N 1/36 |
| 151689 | 8/1985 | European Pat. Off. | A61G 1/36 |
| 256617 | 2/1988 | European Pat. Off. | A61N 1/365 |
| 178528 | 4/1988 | European Pat. Off. | A61N 1/365 |
| 299208 | 1/1989 | European Pat. Off. | A61G 1/365 |
| 361517 | 4/1990 | European Pat. Off. | A61N 1/365 |
| 90/08569 | 8/1990 | PCT Int'l Appl. | A61N 1/00 |

Primary Examiner—William E. Kamm
Assistant Examiner—Scott M. Getzow
Attorney, Agent, or Firm—Davis Hoxie Faithfull & Hapgood

[57] ABSTRACT

A cardiac pacemaker having a pacing rate responsive to a control function of a physiological parameter indicative of activity levels. The coefficients of the function are automatically calculated and modified in response to the trend of the measured physiological parameter in order to correspond to the patient real needs. For monitoring the physiological parameter minute ventilation (VE), the basic value VE low and maximum value VE max are calculated in order to vary the slope and intercept of the straight line representative of the control relation of the pacing rate FC by the minute volume VE.

60 Claims, 8 Drawing Sheets

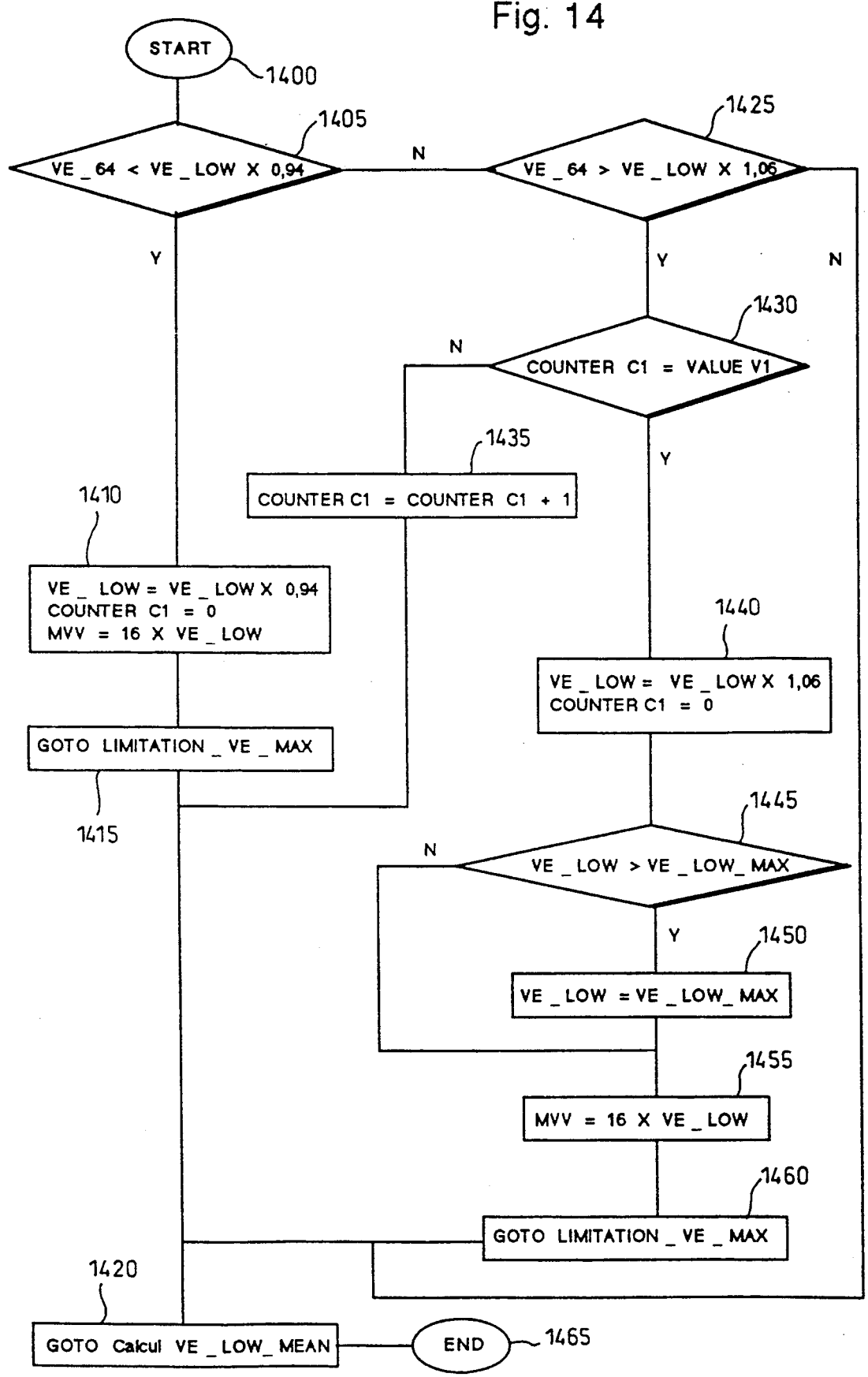

AUTOMATIC ADJUSTMENT OF THE CONTROL FUNCTION FOR A RATE ADAPTIVE PACEMAKER

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

FIELD OF THE INVENTION

The present invention relates to pacemakers having a pacing rate responsive to a monitored physiological parameter related to patient activity, more particularly to adjusting and modifying the control function relating the monitored physiological parameter to the pacing rate in response to changes in the patient's activity range.

BACKGROUND OF THE INVENTION

If the pacing rate of a pacemaker is maintained constant, the patient could not react in an optimum manner during both rest periods and effort periods, i.e., where the patient's level of activity is greater than at rest. Rate adaptive pacemakers typically modify the pacing rate, between a programmed maximum rate and a programmed minimum rate, based on a measure of a physiological parameter of the patient that is related to the patient s activity level. Such suitable physiological parameters that provide a measure of the physical activity of the patient include, e.g., blood temperature, cardiac output, the QT interval, the right ventricle oxygen saturation, respiration rate, and minute volume (also known as minute ventilation).

The minute volume is a physiological parameter that is known to vary linearly with the consumption of oxygen and therefore with the heart rate. The pacing rate (FC) is thus calculated by the pacemaker in accordance with a control function that relates the measure of minute volume (VE) and pacing rate FC via the linear relation: $FC = a(VE) + b$.

When initializing a rate adaptive pacemaker, it is necessary to provide coefficient values for the control function, for example, coefficients a and b of a linear function. In a usual manner, the coefficients are defined when implanting the pacemaker in the patient based on effort tests carried out in a hospital.

Document EP-0 151 689 refers to a pacemaker that uses the minute volume as representative of the activity of the patient and a straight line, linear control function relating the pacing rate and the minute volume. The straight line has a slope that is programmed by the physician based on an assessment of the patient's condition. Thus, the heart pacing rate varies between a programmed minimum pacing rate and a programmed maximum pacing rate as a function of the variations of the sensed minute volume according to the selected slope.

Document EP-0 299 208 refers to a pacemaker of this type in which the straight line representative of the pacing rate as a function of the signal received by the sensor of a physiological parameter is defined by means of two effort tests of the patient. The two tests are performed under different activity conditions, e.g., at rest and at a maximum effort level. These tests define the slope corresponding to the maximum minute volume and maximum pacing rate and the minute volume measure at rest and minimum pacing rate.

One problem with these techniques is that the control function is essentially fixed at implantation and does not allow for variations in the range of the patient's activity levels as in sleep, the starting again of an activity, and the practice of a sport. Another problem is that initialization is based on a medical assessment or controlled effort tests that are not representative of normal life. Consequently, the pacemaker may not provide a pacing rate to support all of the patient's activity. A further problem is that the function can be modified only by a further intervention of the physician and reprogramming of the pacemaker, e.g., in response to additional tests.

There is thus a continuing need to provide for improved rate adaptive pacemakers for pacing the heart as a function of a monitored physiological parameter. There is a further need for modifying the control functions relating the physiological parameter to the pacing rate based on recent patient activity without requiring intervention by the physician.

SUMMARY OF THE INVENTION

It is, therefore, an object of the present invention to provide a rate adaptive pacemaker having a control function that is automatically calibrated in response to recent measures of a physiological parameter.

It is yet another object of the present invention to control a pacemaker having a linear control function relating a physiological parameter to the pacing rate by automatically modifying the slope and intercept of the linear function while it is operating. It is another object to provide an improved rate adaptive pacemaker that adjusts the pacing rate in response to the patient's measured minute volume.

It is another object of the present invention to provide a pacemaker capable of automatically controlling the coefficients of a control function relating a measure of the physiological parameter to the pacing rate at any moment.

The present invention provides improved control over the pacing rate provided by a pacemaker as a function of a monitored physiological parameter representative of the patient's activity level so that the pacing rate corresponds to the patient's activity level at any time. Broadly, the invention concerns apparatus and methods for monitoring relative changes in the sensed values of the physiological parameter over one or more preselected periods of time and modifying the control function in response to changes so that the maximum pacing rate is related to the patient's sensed physiological parameter corresponding to the recent maximum activity level and the minimum pacing rate is related to the patient's sensed physiological parameter corresponding to the recent minimum activity level.

One aspect of the invention is directed towards a method for controlling a pacemaker having a pacing rate (FC) that is controlled as a function of a sensed physiological parameter (X) of the patient, wherein the function includes coefficients which are, at any moment and in an automatic manner, calculated and possibly modified, based on preselected maximum and minimum pacing rates and the sensed maximum and minimum physiological parameters. Preferably, the maximum and minimum pacing rates, FC max and FC low, respectively, are conventionally defined and programmed by the physician and the minimum and maximum physiological parameters X low and X max, respectively, are automatically calculated based on a measure of the physiological parameter so that the control function is defined by two end points (FC low, X low) and (FC max, X max).

In a preferred embodiment, the control function is linear such that FC=a(X)+b, and having a slope and intercept defined by two pairs of values: (FC low, X low) and (FC max, X max).

In accordance with a preferred embodiment, the values X low and X max are initialized and thereafter recalculated automatically, based on recently sensed physiological data. Thus, the values X low and X max may be recalculated at any moment in response to sensed changes in activity. For example, the X low value may be periodically compared to a first measure representative of the patient's recent minimum activity levels, e.g., a long term average of the parameter measure, and the X max value may be periodically compared to a second measure of the parameter representative of the patient's recent maximum activity levels, e.g., a short term average of the parameter or measure. The control function is subsequently calibrated to the updated endpoints so that the pacing rate corresponds to the real activity needs of the patient at any time.

In a preferred embodiment the control function is initialized by calculating X low and X max based on a first measure of the physiological parameter, e.g., minute volume. Preferably, the first measure is obtained while the patient is in a sustained rest activity condition and the term X low is set equal to the first measure. The term X max may then be set as a function of X low.

For example, the control function for minute volume may be initialized by calculating an initial VE low based on the mean value of the measured minute volume VE taken over a number of successive breathing cycles while the patient is at rest. An initial VE max may be calculated as a multiple of the measure used for VE low. The number of cycles at rest may be between 16 and 64 cycles, preferably 32. The multiplier for VE max is preferably 6.

Alternatively, initialization may occur either by providing a first value that is either a hypothetical or generic activity level corresponding to rest or normal activities or a first value based on a sensed time measure of the physiological parameter. In this alternative procedure, the first value is used as the initial X low value and the X max value is calculated as a function of the X low value (or vise versa) and the pacemaker begins recalculating the X low and X max values in response to subsequently obtained physiological data until the values of X low and X max have stabilized. Thereafter, pacing in accordance with the calibrated control function as adjusted in accordance with the invention will occur. In this process, the pacemaker may be provided with an alternate pacing mode that is not based on the physiological parameter for pacing the patient's heart until the auto initialization provides relatively stable values X low and X high relative to the patient's actual activity range. Thus, an automatic adjustment period of a few hours, days or weeks to bring the provided first value to a minimum (or maximum) activity level, during which time the alternate pacing mode operates, will pose no risk to the patient.

In a preferred embodiment, the physiological parameter X is the minute volume VE such that X low is VE low and X max is VE max. Preferably, a measure of minute volume VE is obtained each breathing cycle and procedures are provided for increasing and decreasing the initialized (and any subsequently calculated) VE low and VE max coefficients based on recently sensed minute volume data.

Regarding adjustment of the maximum activity value VE max, a first activity value corresponding to a short term average of the physiological parameter is obtained. Preferably, a mean value VE/N is calculated using the VE measures obtained over the last N breathing cycles and compared to the then existing value of VE max during use. If VE/N is less than the value of VE max, VE max is not adjusted. If VE/N is higher than VE max, the value of VE max will be modified to reflect the higher actual activity level. Preferably, the VE max value will be updated to be the smallest of either the value VE/N or the value Z(VE max), with Z being a constant selected from between 1.03 and 1.12, preferably 1.06. N is preferably a number selected from between 4 and 16, preferably 8.

This adjustment technique provides for gradually increasing the maximum activity value VE max and so that very short term high effort levels and artifacts will not radically change the pacing rate for the same actual activity level at different times.

In addition, the value of VE max is lowered by an amount of the order of 3% to 6% of its value, and preferably 3%, if the value of VE max has not been modified during a defined period on the order of from 12 to 48 hours, preferably 24 hours. This provides for the maximum activity value to decrease gradually until it closely tracks the actual sensed maximum activity that would increase the value VE max. It also corrects for a long term decrease in the patient's recent activity.

The value of VE max is preferably controlled to be within between calculated upper and lower limits. For example, the upper limit may be based on the theoretical maximum value of the patient's ventilation (MVV) and selected to be sixteen times the minimum activity value VE low. The lower limit may be a multiple Y of the minimum activity value VE low such that Y=2, 3, 4, 5 and may be programmed by the physician. These limits provide for always maintaining a VE max within a prescribed range of VE low. Thus, for example, a patient who is inactive for several days will still have distinct VE low and VE max values, even though there has been no recent effort. The maximum limit is practical in that a person can only sustain maximum effort for a limited time.

In the preferred embodiment, the control function is recalculated after each modification of the term VE max as soon as the heart rate of the patient falls below a threshold rate defined close to the basic rate. This provides for preventing erratic jumps in the pacing rate which might result if the control function were adjusted during effort. In as much as changes in the minimum activity level typically occur over longer periods of time, the recalculation of the control function need only occur when VE max is adjusted, and not when VE low is adjusted.

Regarding adjustment of the minimum activity level value VE low, a second activity value corresponding to a longer term average of the physiological parameter is obtained. Preferably a mean value VE/M is calculated based on VE measures obtained during M preceding breathing cycles, such that VE/M is calculated every M/2 breathing cycles. The mean value VE/M is compared to VE low$\pm$x%, with x being selected to be between 3 and 9, preferably 6. VE low is adjusted to have a new value of VE low−x% if VE/M is less than VE low−x%. VE low is adjusted to have a new value VE low+x% if the measure of VE/M exceeds the value VE low+x% for more than a selected number of threshold crossings (referred to as overshootings of the threshold) e.g., between 4 and 12, preferably 8, during which time VE low has not been adjusted. The number of overshootings of the threshold need not be consecutive.

Preferably, the value VE low has a maximum limit VE low/max. This limit is calculated to be a y% increase of a value VE low/mean, wherein the term VE low/mean is equal to the mean value of VE low noted every P breathing cycles, where P is selected from between 48 and 192, preferably 96, and y is selected from between 10 and 30 and preferably 20. More preferably, the mean value VE low/mean is of 256 values of VE low noted every 96 breathing cycles (that is, VE low/mean is calculated every 24576 breathing cycles or about a day).

BRIEF DESCRIPTION OF THE DRAWINGS

Further features of the invention, its nature and various advantages will be more apparent from the accompanying drawings and the following detailed description of the invention, in which like reference numerals and characters refer to like elements and parameters, and in which:

FIG. 14 is a logical diagram for the Calculate Low Point routine VE low in accordance with an embodiment of the present invention.

DETAILED DESCRIPTION OF THE INVENTION

With reference to FIGS. 1–15, the present invention relates to a pacemaker that responds to a measure of a physiological parameter representative of the activity of the patient. In accordance with the preferred embodiment of the invention, and referring to FIG. 10, no parameter related to the maximum and minimum levels of the physiological parameter x, representing maximum or minimum levels of patient activity are programmed. Instead, only the basic (or minimum) heart pacing rate FC low and the maximum heart pacing rate FC max are programmed according to the patient. Thereafter, the control function coefficients are calibrated to the sensed physiological parameter using predetermined interrelationships and a provided activity value to initialize the calculation. Preferably, the provided activity value is an acquired physiological value, more preferably a measure corresponding to rest activity. Thereafter, the coefficients are continuously revalued and modified as further physiological data is acquired to correspond to the activity levels represented by such data.

As a result, the control function is automatically recalibrated as recently acquired physiological data reflects changes from the previously acquired data to provide an automatically calibrated relation between the monitored physiological parameter reflecting current activity and the pacing rate that is as close as possible to the metabolic needs of the patient. In other words, by adjusting the control function based on recently acquired data, the cardiac pacing rate is maintained adequate for the historically likely, instantaneous activity needs of the patient.

In a preferred embodiment, the physiological parameter is taken as a measure of the minute volume (VE), which may be an arbitrary unit, corresponding to the volume of air expired by the patient in one minute. The corresponding control function is a line representative of the relation between the measured minute volume VE and the pacing rate FC. In accordance with the invention, the line is adjusted between endpoints of the cardiac rate limits and the calibrated maximum and minimum activity values as the activity values change from time to time.

Figure 1:
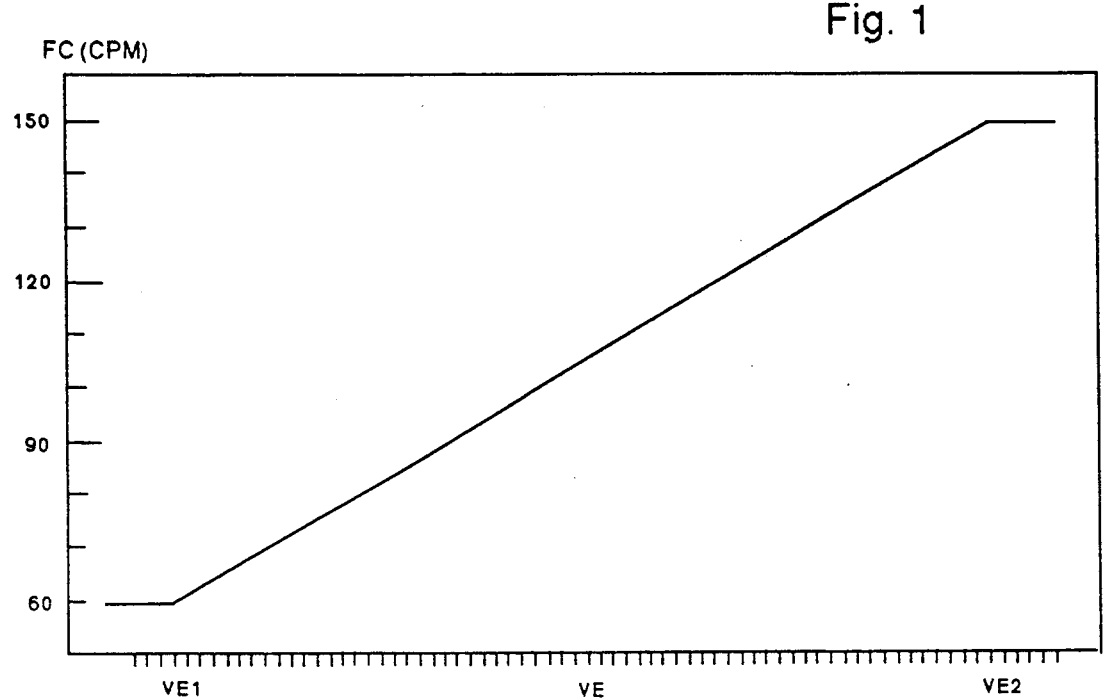
FIG. 1 is a calibration curve representative of a linear function relating the arbitrarily calculated minute volume VE and the heart pacing rate FC in cycles per minute (cpm)

In FIG. 1, the calibration curve is a linear relation relating the minute volume measure, preferably an average of M measures calculated every Mth cycle, such that M is between 2 and 16, more preferably an average over 4 breathing cycles (referred to as "VE/4") and the control pacing rate FC. The pacing rate FC has a programmed minimum pacing rate of 60 and a programmed maximum pacing rate of 150 beats per minute. For a minute volume less than the low point VE 1, the heart is paced at the programmed basic rate FC low. Similarly, for a minute volume value greater than the high point VE 2, the heart is paced at the programmed maximum rate FC max. Between the two points the heart rate is calculated as a linear interpolation of the end points (VE max, FC max) and (VE low, FC low), determined according to the invention, and the measured average minute volume VE/4.

The minute volume parameter may be obtained by any suitable technique. One such technique is to implant an endocardial lead in the right heart, inject a pulsatile current (e.g., 15 microsecond pulses having an amplitude of 400 microamps at a repetition rate of 8 Hz) in the heart and measure the transthoracic impedance variations. One conventional bipolar lead is Model T84, available from Ela Medical, Montrouge, France. Frequencies not related to the respiratory impedance variations, are filtered out using a bandpass filter having a low pass filter at 0.5-0.75 Hz and a high pass filter at 0.05 Hz. The respiratory impedance maximum and minimum values and frequency variations over time are converted into a parameter VE representing volume of air per minute in a known manner. The resultant measure is then received for processing in accordance with the present invention.

Alternate techniques for acquiring minute ventilation and selecting a calculated cardiac stimulation rate may, of course, be used. See for example, U.S. Pat. Nos. 4,901,725, 4,702,253 and 4,596,251. The conversion of transthoric impedance variations into a minute volume measure is known. The apparatus and methods for acquiring and calculating the measure of a physiological parameter, in particular the minute volume are known and form no part of the present invention.

Figure 10:
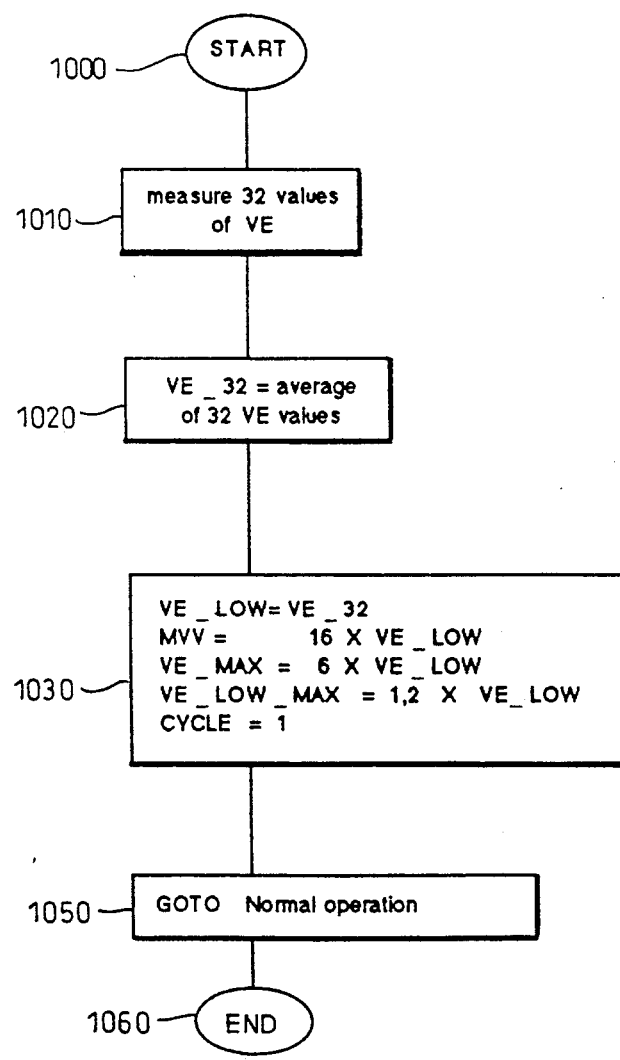
FIG. 10 is a logical diagram of the Initialization routine in accordance with an embodiment of the present invention.

Referring to FIG. 10, once the pacemaker is programmed with FC max and FC low, the high and low values of the minute volume VE max and VE low are initialized. Following initialization, the values VE max and VE low are then automatically adjusted as new minute volume measures are acquired and evaluated according to the invention.

Initialization concerns providing initial parameters for VE low and VE max for defining the initial slope and intercept of the control function. In a preferred embodiment, initialization occurs by placing the patient in a rest activity level so that the system obtains an average VE/N of the minute volume measures VE during N breathing cycles while the patient remains at rest, such that N=32 and the average value is VE/32. The low minute volume value VE low is then initialized to be equal to the calculated mean value VE/32.

The high minute volume value VE max is initialized by setting VE max equal to 6 times VE low. The multiplier 6 is a preferred value that is selected to take into account the fact that the theoretical maximal value of the minute volume MVV, which in practice is almost never reached by a person in normal life, is between 10 and 12 times that of the minute volume at rest. It is generally understood that the maximum minute volume reached during the normal range of activities is generally between 25 and 50% of the theoretical maximum value. Accordingly, VE max is a priori selected to be equal to 6 times VE low. Other multiplier numbers could of course be used.

Thereafter, the system defines then a straight line representing the linear control function relating the pacing rate FC and the minute volume VE based on the programmed FC low, FC max, the initialized VE low and VE max. This line is represented at slope 1 in FIG. 9, and will be used to control the pacing rate in response to each calculated value of VE acquired.

According to the invention, the pacemaker will, at any moment during its operation, recalibrate and modify if necessary the values VE low and VE max. When the control function is adjusted to reflect changes in VE low and VE max, the result is a pacing rate FC that is maintained as close as possible to the effort state of the patient and the patient's metabolic need.

For example, if the patient is in a phase of effort, i.e., a level of activity that is above a threshold level of activity corresponding to rest, the pacing rate FC should accelerate so as to ensure a sufficient oxygenation of the blood. If the patient is stopping this effort, i.e., in a recovery phase where the level of activity is decreasing, e.g., to the rest level, the rate FC should then be reduced little by little while the minute volume is still at a high level, but decreasing. The control function slope and intercept will be recalculated once the VE max term has been adjusted and following the pacing rate FC falling below a threshold using the then existing values of VE max (which has been adjusted) and VE low (which may or may not have been adjusted).

The following description relates first to the automatic calibration of VE max which tends to bring VE max close to the real value of the maximum minute volume of the patient.

The minute volume VE of the patient is measured at each breathing cycle. A mean value over the 8 last VE measures, referred to as "VE/8", is calculated every 8 breathing cycles, and is compared to the present value of VE max. If the mean calculated value VE/8 is greater than VE max, then VE max is increased by up to an amount in the range of between 3% and 12%, preferably 6% of the old value. Preferably, this is accomplished by multiplying the existing VE max by a value selected from between 1.03 to 1.12, and replacing the prior VE max value with the smallest of either the value VE/8 or the value 1.06 times VE max. By this procedure, the value VE max will follow an increasing minute volume measure but will not overshoot the maximum sensed minute volume by more than the selected percent. If the calculated value VE/8 is less than VE max, the value of VE max is not modified by this routine.

Figure 2:
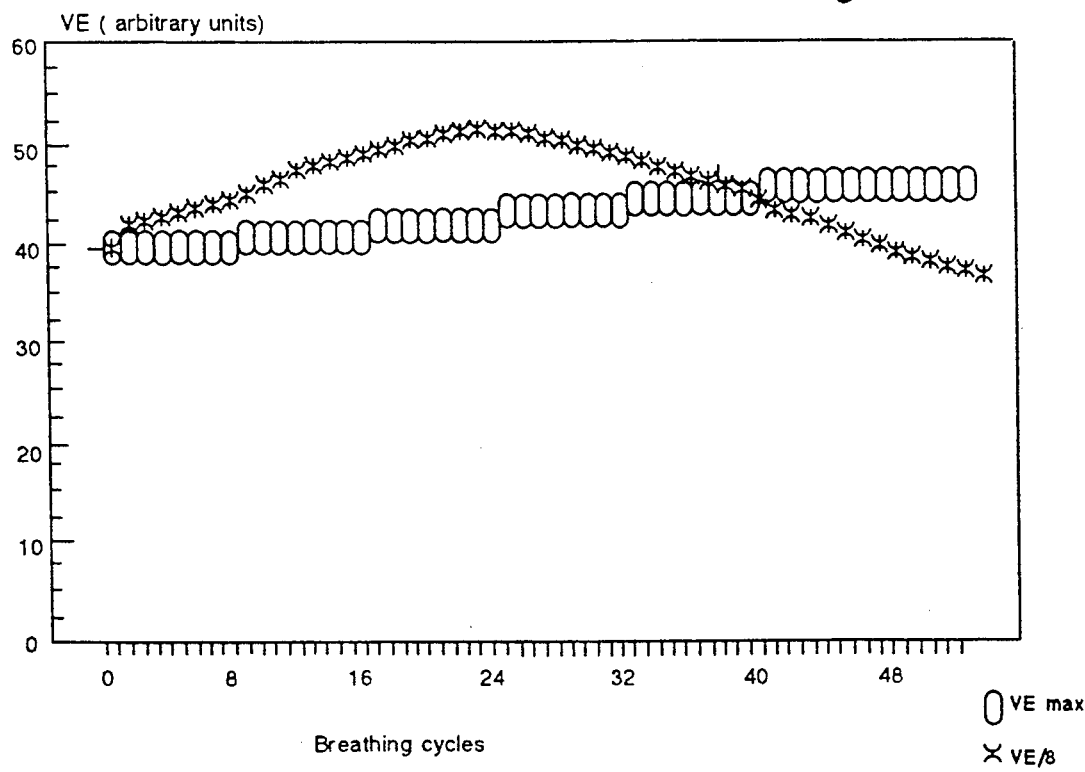
FIG. 2 is a plot in arbitrary units of the measure of the minute volume parameters for the mean value VE/8 and the change in the value of VE max versus breathing cycles.

Referring to FIG. 2, every 8 breathing cycles, the value VE/8 is compared with the existing value VE max. If VE/8 is greater than VE max, VE max is increased by 6% as described. During a large effort, VE max can be increased by 6% consecutively.

The value of VE max also will be adjusted if it is not otherwise adjusted during a preselected time period of from 12 to 48 hours, preferably 24 hours. If VE max is not adjusted during this time, then at the end of the period VE max is automatically reduced by a selected amount, e.g., between 3% and 6%, preferably 3%.

Following any modification of the value of VE max, the new value is evaluated to check that the new VE max value remains within a defined range. This range has for an upper limit the theoretical maximal value of the ventilation MVV, which is 16 times the current value of VE low. The lower limit of VE max is defined by the physician who programs a value Y such that the lower limit of VE max is set equal to (Y)*(VE low) wherein Y is one of 2, 3, 4 or 5, according to the physical condition of the patient. This is provided so that VE max does not descend too low when there is an extended period of inactivity. Thus, if the new value of VE max becomes greater than the limit MVV, its value is set to MVV and if it becomes less than the defined minimum threshold, its value is set to equal the value of the minimum threshold. It is noted that as the value VE low is adjusted, the values against which changes in VE max are compared are also accordingly adjusted.

As noted, when VE max is modified, the relation calibrating the pacing rate FC to the minute volume VE is not immediately recalculated. Rather, it is first determined that the patient is not exerting an effort which could still increase the breathing and therefore VE max, to a higher value. The control relation between FC and VE is then recalculated when the patient has ceased any effort. The return to rest is defined when the pacing rate FC has become less than a selected threshold rate. Preferably, the period of the threshold is defined as being equal to the basic period FC low, and the threshold rate is equal to 60,000/(threshold period) when the period is expressed as an interval in milliseconds.

Figure 3:
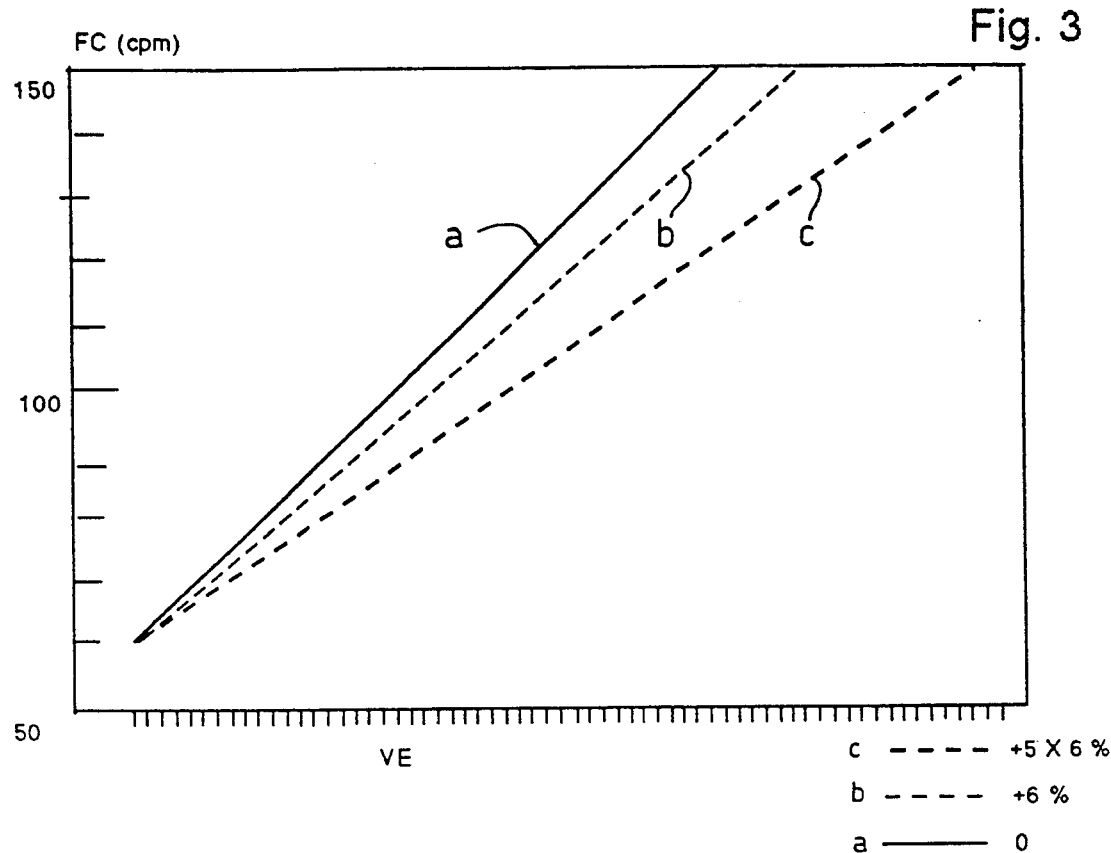
FIG. 3 is a plot relating the pacing rate FC in cycles per minute (cpm) to the arbitrary unit measure of minute volume VE representative of two relative adjustments of the control function after recalibration of the high point VE max.

Referring to FIG. 3, as soon as the patient returns to a rest state, a new calibration slope is selected if the high point VE max has been modified. Three slopes a, b, and c are shown corresponding to no change in VE max, an increase by 6% and 5 successive increases of 6%, respectively.

Figure 4:
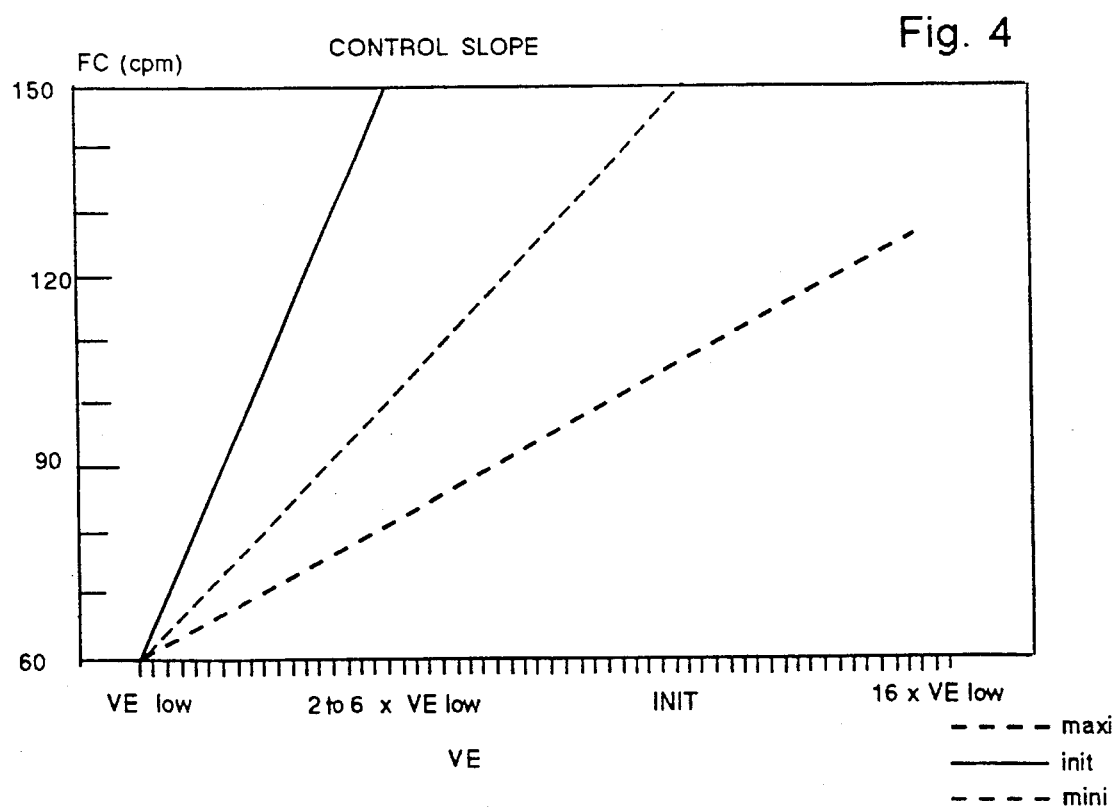
FIG. 4 is a plot of the changes in the control function relating the pacing rate FC in cycles per minute to the arbitrary unit measure of minute volume VE representative of various control slopes when in an automatic recalibration.

Referring to FIG. 4, in an automatic calibration, the high point VE max can change freely according to the recent activity of the patient and between 16 times the low point VE low and the programmed low threshold value of Y times the low point VE low.

Referring to FIGS. 5-8, the automatic calibration of VE low will now be described. Experience has indicated that the minute volume at rest varies very little. Typically, its modifications are either of short duration, or due to a long term evolution generated by an illness or an aging of the patient, or due to electrical modifications, e.g., of the endocardial lead due to fibrosis. In addition, the calibration system must be able to distinguish between a continuous and extended effort and an increase of the minute volume at rest.

According to the present invention, the value VE low is determined as follows. Every 32 breathing cycles, a mean value VE/64 is calculated based on the VE measures acquired during the 64 preceding cycles. The value VE/64 is then compared to two thresholds, VE low−6% and VE low+6%.

Figure 5:
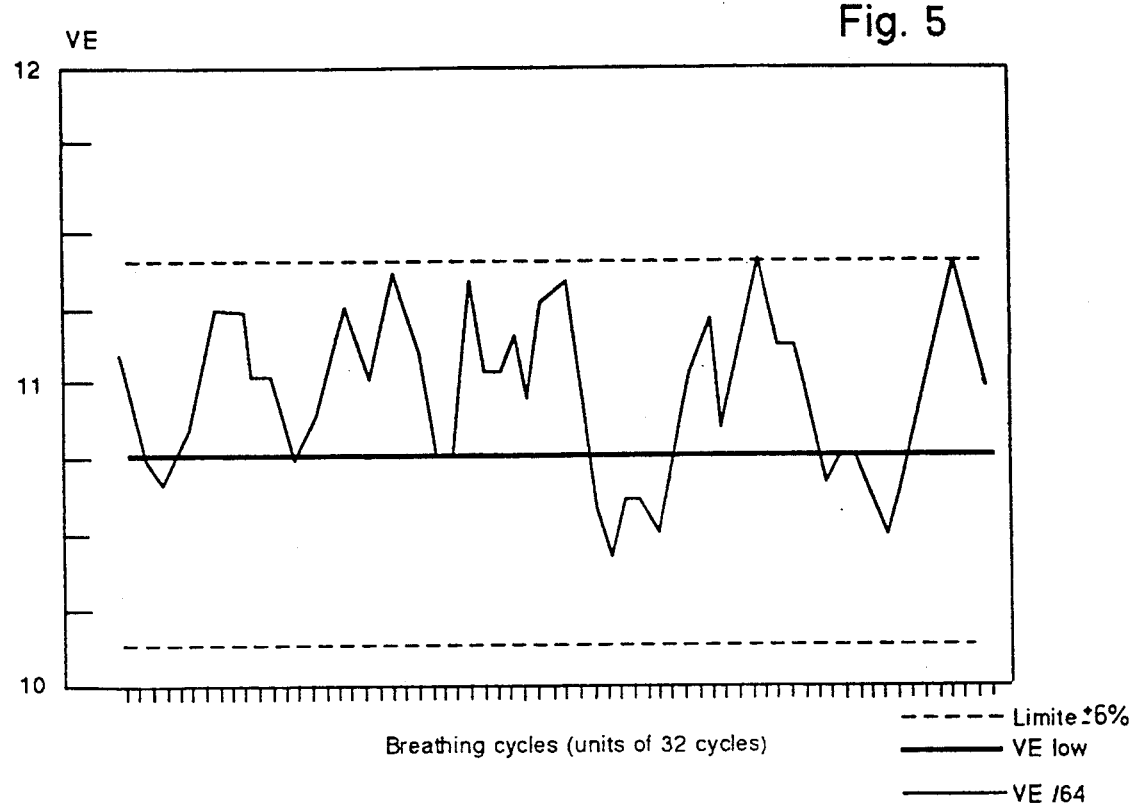
FIG. 5 is a plot of the arbitrary unit measure of minute volume VE versus breathing cycles (scale is 32 breathing cycles per division) illustrating the upper and lower limit thresholds for VE low and the mean value VE/64.

Referring to FIG. 5, if VE/64 remains within the threshold range (VE low±6%), VE low is not modified. This provides for not modifying VE low for slight variations.

Figure 6:
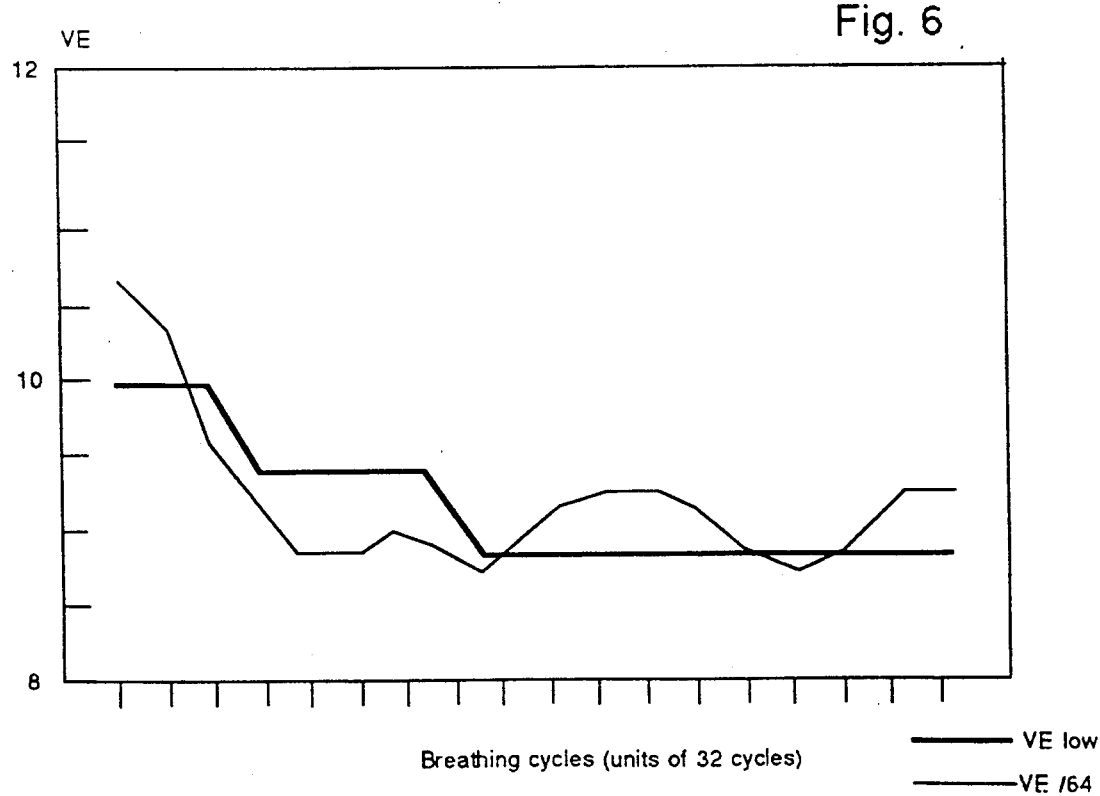
FIG. 6 is a plot of the arbitrary unit measure of minute volume VE versus breathing cycles (scale is 32 breathing cycles per division) showing the descent of VE low point relative to VE/64.

If, however, VE/64 is less than VE low−6%, it is determined that the ventilation at rest has come down and VE low is adjusted to be the value of VE low−6%, that is, 6% below the preceding VE low. Referring to FIG. 6, as soon as VE/64 is below the low threshold, VE low is decreased by 6%.

Figure 7:
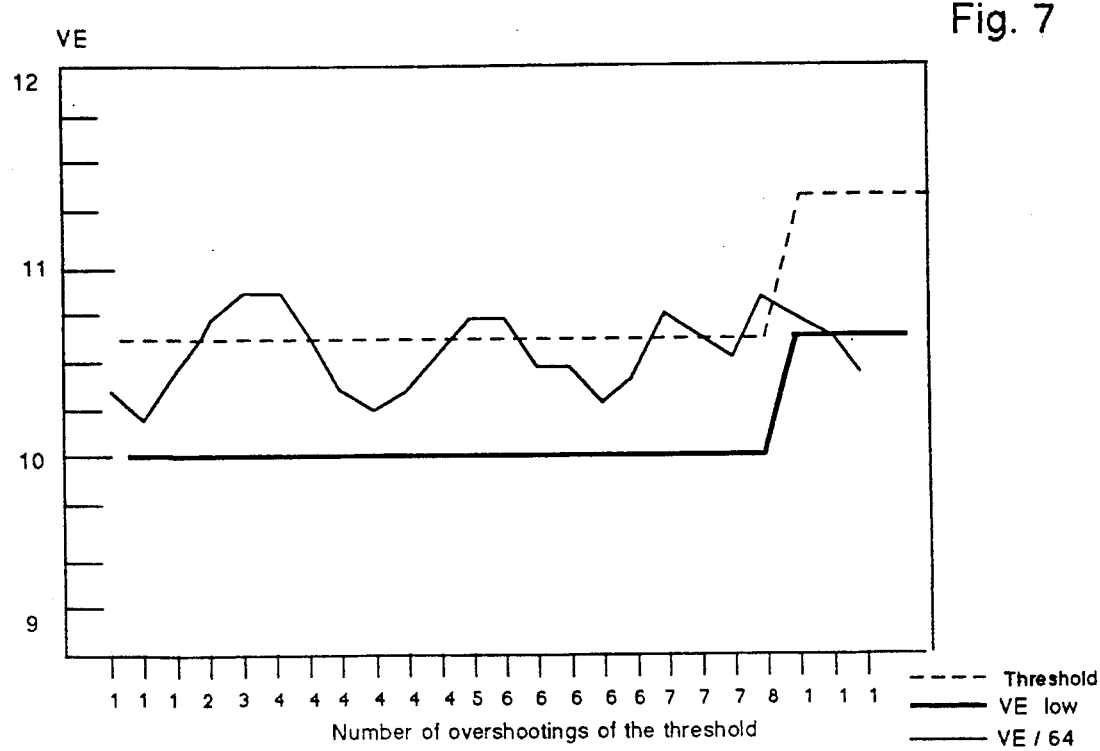
FIG. 7 is a plot of the arbitrary unit measure of minute volume versus breathing cycles showing the mean value VE/64 relative to VE low and the ascent of VE low after 8 overshootings of the threshold.
Figure 8:
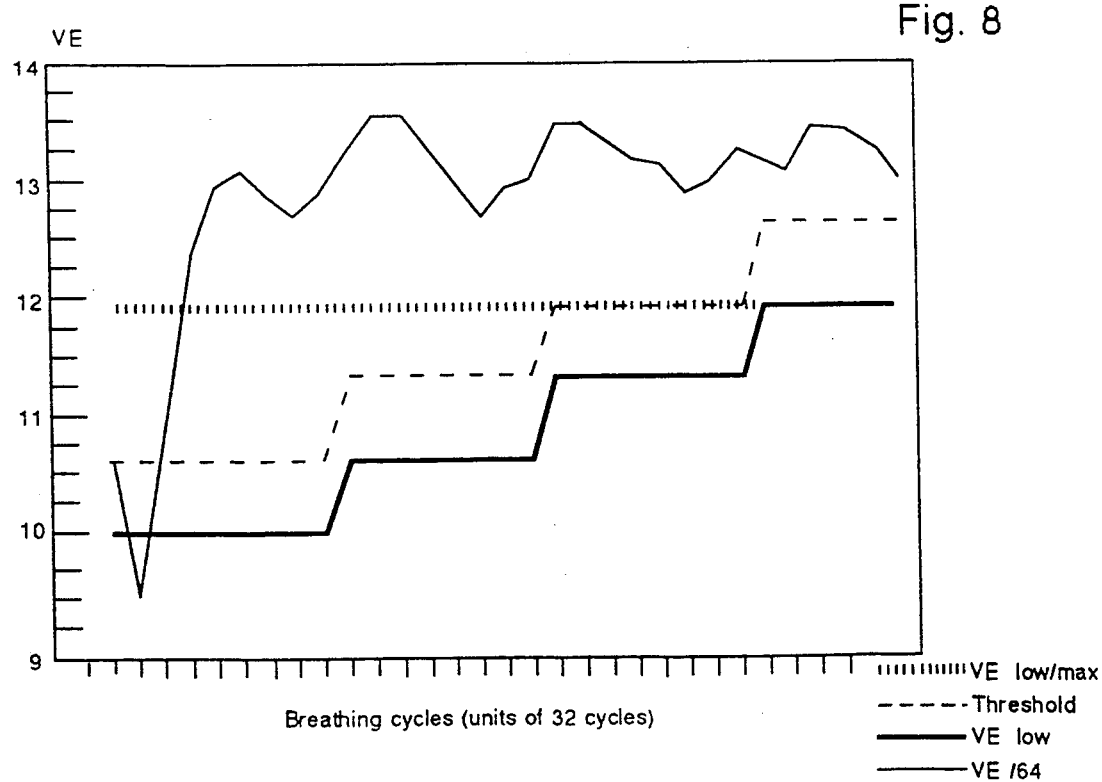
FIG. 8 is a plot of the arbitrary unit measure of minute volume VE versus breathing cycles (scale is 32 breathing cycles per division), showing the mean value VE/64 relative to VE low and the threshold, and showing the limitation of the ascent of VE low relative to the value VE low/max.

If VE/64 is greater than the upper threshold VE low+6%, the duration of the increase is checked before increasing VE low. This is to distinguish effort from an increased rest level. In the preferred embodiment, one increments a counter one time for each breathing cycle that VE/64 is above VE low+6%. As soon as the counter reaches 8, meaning that the value of VE/64 has been greater than VE low+6% for 8 comparisons over 256 breathing cycles and VE low has not been adjusted, then VE low is increased by 6% (FIG. 7). In this embodiment, the counter is reset to zero whenever the value of VE low is reduced or increased (see FIG. 6).

Preferably, during any modification of VE low, the new value is evaluated to determine whether it remains below a maximum value VE low/max, which is preferably calculated every day (or periodically).

In this regard, every 96 breathing cycles, the value VE low/mean over the 96 cycles is memorized. Then the mean value VE low/mean of 256 such values is calculated. This value VE low/mean is therefore calculated every 24576 breathing cycles, corresponding to about a day.

The value VE low/max is then defined as being y% larger than the calculated VE low/mean where y is between 10 and 30, preferably 20. For y=20, VE low/max=1.2*(VE low/mean). VE low/max is thus calculated as the maximum value which can be assumed by VE low regardless of the value of VE/64 (see FIG. 8). Every 32 cycles VE low is checked to see if it has exceeded the value of VE low/max.

Whenever VE low is modified, one recalculates the term MVV which is used for calculating whether VE max is within the imposed limits.

Figure 9:
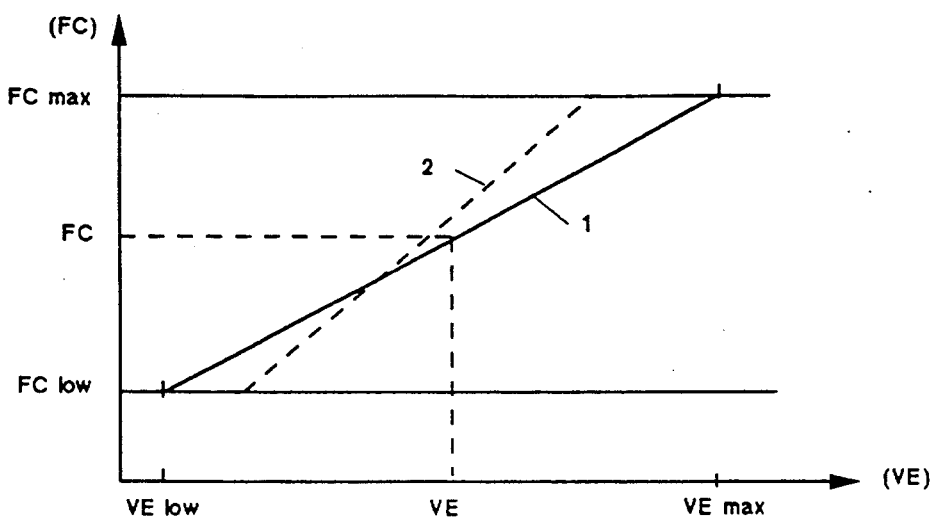
FIG. 9 is a plot of the pacing rate FC versus minute volume VE showing an adjustment of the control function having slope 1 and slope 2 between VE max and VE low calculated in accordance with the present invention.

Referring to FIG. 9, the line slope 2 shows an example of the control relation between the pacing rate FC and the minute volume VE after modification of the values of VE low and VE max.

Referring to FIGS. 10-15, and the software program language description and code appended hereto, a preferred embodiment of the present invention for adjusting the control function of a rate adaptive pacemaker is now described with reference to the relationships illustrated in FIGS. 1-8.

Referring to FIG. 10, Routine INITIALIZATION begins at 1000 and proceeds to box 1010 where 32 measures of the patient's minute volume VE with the patient at a rest condition are acquired. Thereafter, the routine proceeds to box 1020 where the value VE/32 is formed as the average of the 32 acquired VE measures. Next, the routine proceeds to box 1030 where the value of VE low is initialized to be equal to VE/32, the term MVV is initialized to be equal to 16×VE low, the term VE max is initialized to be equal to 6×VE low, the term VE low/max is initialized to be equal to 1.2×VE low and the counter CYCLE is set to 1. Following initialization of the parameters, the routine passes to box 1040 and the Routine NORMAL OPERATION.

Figure 11:
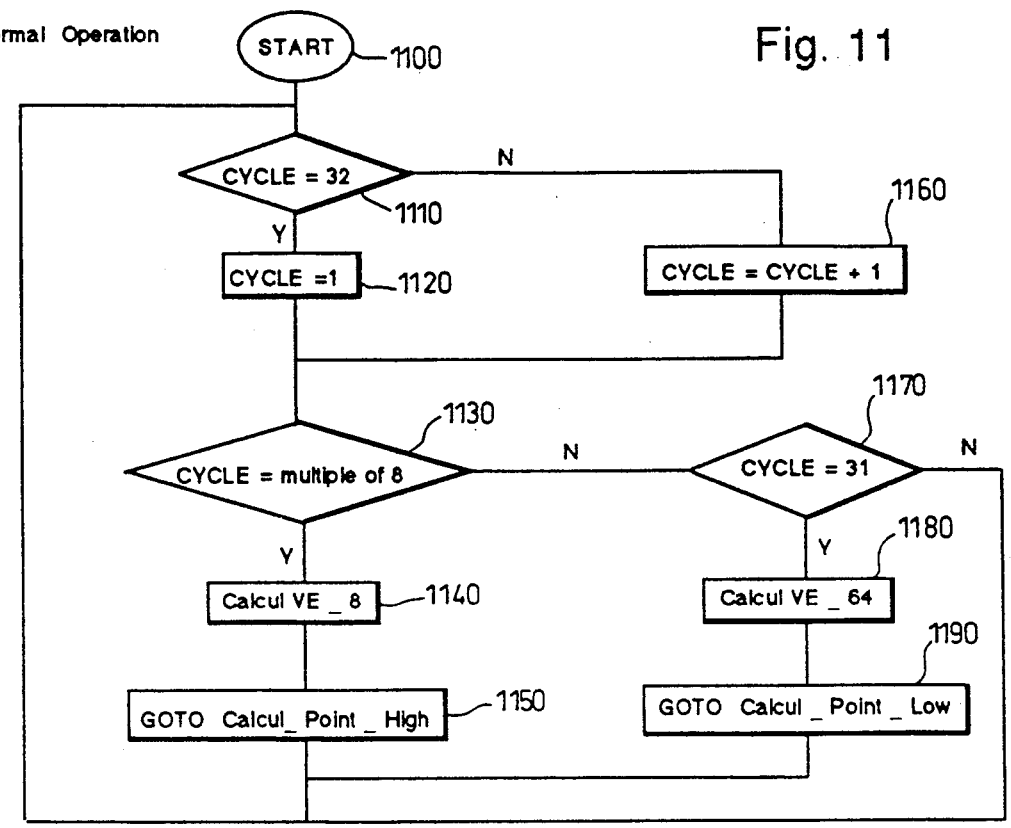
FIG. 11 is a logical diagram of the Normal Operation routine in accordance with an embodiment of the present invention.

Referring to FIG. 11, Routine NORMAL OPERATION is a system level processing loop for monitoring changes in minute volume and adjusting the parameters of the control function accordingly. The routine is entered at 1100 from routine INITIALIZATION and proceeds to determine at 1110 whether the counter CYCLE is set to 32 corresponding to 32 breathing cycles having occurred. If they have not, then the counter CYCLE is incremented at 1160 and the routine passes to box 1130 where the counter CYCLE is queried to determine whether it is a multiple of eight. If CYCLE is set to 32 at box 1110, then the routine resets CYCLE to 1 at 1120 and proceeds to box 1130 as described. If CYCLE is a multiple of eight, then a value VE/8 is calculated at box 1140 as the average of the last eight measures of minute volume VE. Following calculation of VE/8, the routine passes to box 1150 and the Routine CALCULATE HIGH POINT. If CYCLE is not a multiple of eight, then it is queried at box 1170 whether it is set to 31. If CYCLE is set to 31, corresponding to the end of thirty-two consecutive breathing cycles, then the value VE/64 is calculated at box 1180 and the routine passes to box 1190 and the Routine CALCULATE LOW POINT. Following the end of either of Routines CALCULATE HIGH POINT or CALCULATE LOW POINT, the routine resumes its loop processing and returns to box 1110. If CYCLE is not at 31 and is not a multiple of eight, then the routine returns to box 1110 for the next breathing cycle.

Figure 12:
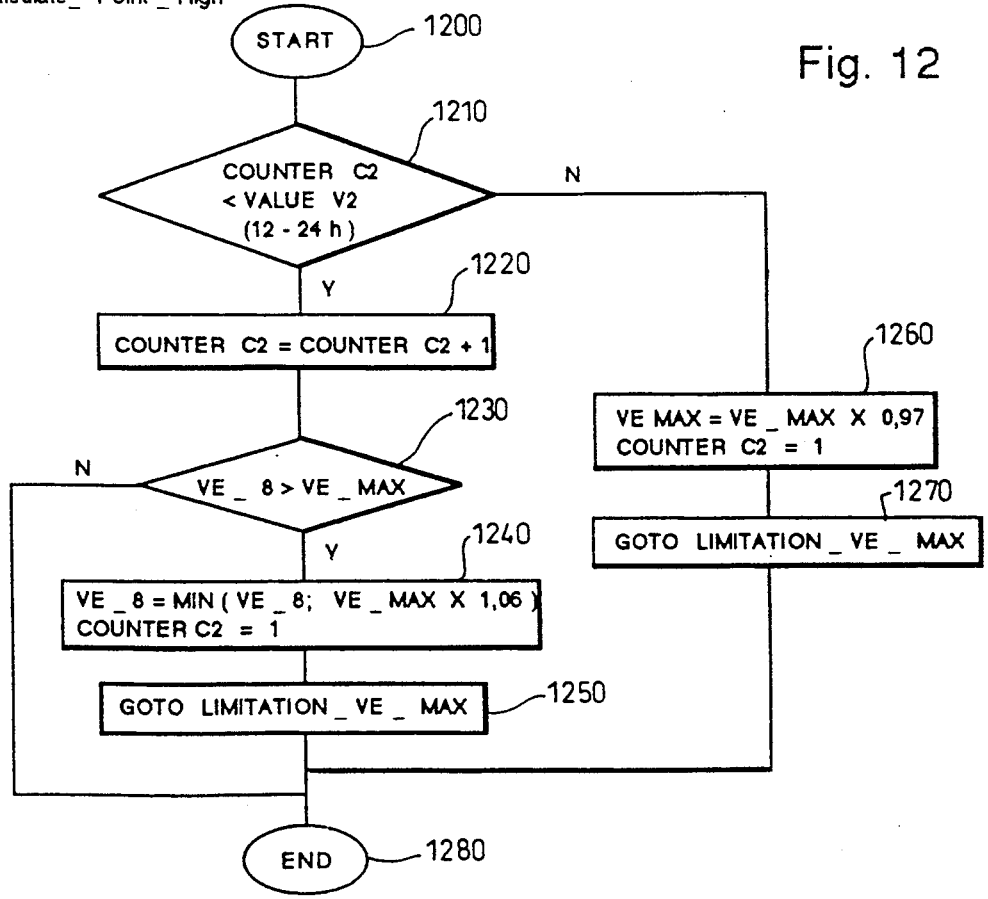
FIG. 12 is a logical diagram of the Calculate High Point VE max routine in accordance with an embodiment of the present invention.

Referring to FIG. 12, the Routine CALCULATE HIGH POINT is entered at 1200 and passes to box 1210 where a counter C2 is compared to a value V2, where the value V2 is selected to correspond to a preselected period on the order of one half to two days, preferably 24 hours. Preferably, value V2 is a digital count of the number of clock cycles that will occur corresponding to a twenty-four hour period. If counter C2 is less than value V2, the routine passes to box 1220 where counter C2 is incremented and to box 1230 where the value VE/8 is compared to the value of VE max, which may be the initialized value or a subsequently calculated value. If VE/8 is not greater than VE max, the routine exits at 1280. If VE/8 is greater than VE max, then VE/8 is adjusted at box 1240 and selected to be equal to the smaller of VE/8 and the value VE max $\times$ 1.06 and the counter C2 is reset to 1. Then, the routine passes to box 1250 and routine LIMIT VE MAX is performed. If counter C2 is at or greater than the value V2 at box 1210, which means that the preselected long time period has passed without VE max being adjusted, then the routine passes to box 1260 where the value VE max is decreased by multiplying the present value times 0.97 and counter C2 is reset to 1. After adjusting VE max, the routine passes to box 1270 and routine LIMIT VE MAX is performed. Following the end of routine LIMIT VE MAX, the routine then exits at 1280 and returns, e.g., to routine NORMAL OPERATION.

Figure 13:
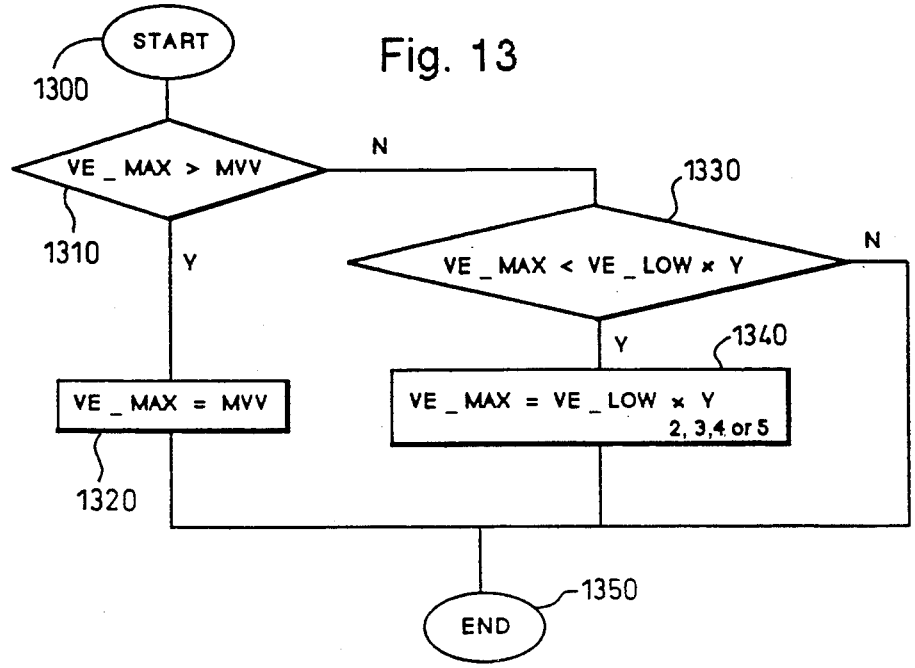
FIG. 13 is a logical diagram for the Calculate Limit VE max routine in accordance with an embodiment of the present invention.

Referring to FIG. 13, the Routine LIMIT VE MAX is entered at 1300, for example, from routine CALCULATE HIGH POINT, and passes to box 1310 where the adjusted value VE max is compared to the term MVV, which may be the initialized parameter or a subsequently adjusted value. If VE max is greater than MVV, the routine passes to box 1320 where VE max is set equal to MVV and exits at routine 1350, for example, to routine CALCULATE HIGH POINT. If VE max is not greater than MVV, the routine passes to box 1330 where VE max is compared to a programmed minimum limit of VE max which is based on the existing value of VE low times a multiplier Y, where the multiplier is programmed by the physician during programming of the pacemaker by, e.g., conventional telemetry, and is selected from between 2 and 6, preferably an integer. The multiplier is provided to provide an initial slope value to the control function and is thereafter programmed based on changes in the VE low term over time. If VE max is less than the minimum limit for VE max, then VE max is set to be equal to the minimum limit at box 1340 and the routine exits at 1350.

Referring to FIG. 14 the Routine CALCULATE LOW POINT is entered at 1400, from, e.g., routine NORMAL OPERATION, and proceeds to box 1405 where the term VE/64 is compared to a minimum limit for VE low corresponding to VE low $\times$ 0.94. If VE low is greater than the minimum limit, then the routine passes to box 1425 where the value VE/64 is compared to a maximum limit for VE low of VE low $\times$ 1.06. The maximum and minimum limits are provided to prevent changing VE low in response to minor changes in the value VE/64. If VE/64 is less than the maximum limit then the routine passes to box 1420 and routine CALCULATE VE low/mean. Following the completion of that routine, routine CALCULATE LOW POINT exits at 1465.

If, however, the value VE/64 is less than the minimum limit at box at box 1405, then the routine CALCULATE HIGH POINT passes to box 1410 where the value of VE low is adjusted to be equal to VE low $\times$ 0.94, the counter C1 is reset to 0 and the term MVV is updated to be 16 $\times$ VE low, using the VE low value just calculated. Thereafter, the routine passes to box 1420 as described above.

If VE/64 is greater than the minimum limit at box 1405 and greater than the maximum limit at box 1425, the routine passes to box 1430 where counter C1 is compared to the preselected value V1 corresponding to 8 crossings of the threshold. If counter C1 is not equal to value V1, then the routine passes to box 1435 where counter C1 is incremented and then to box 1420 as already described. If counter C1 is equal to value V1, then the routine passes to box 1440 where the value VE low is adjusted relative to VE low $\times$ 1.06 and counter C1 is reset to 0. Then the routine passes to box 1445 where the new term VE low is compared to the value VE low/max. If VE low is not greater than VE low/max, the routine passes to box 1455 and the term MVV is adjusted to be equal to the new VE low and the routine passes to box 1460 and routine LIMIT VE MAX. If VE low is greater than VE low/max, then the routine passes to box 1450 where VE low is set equal to the value of VE low/max and then passes to boxes 1455 and 1460 as described. Following the end of routine LIMIT VE MAX, the routine passes to box 1420 as already described.

Figure 15:
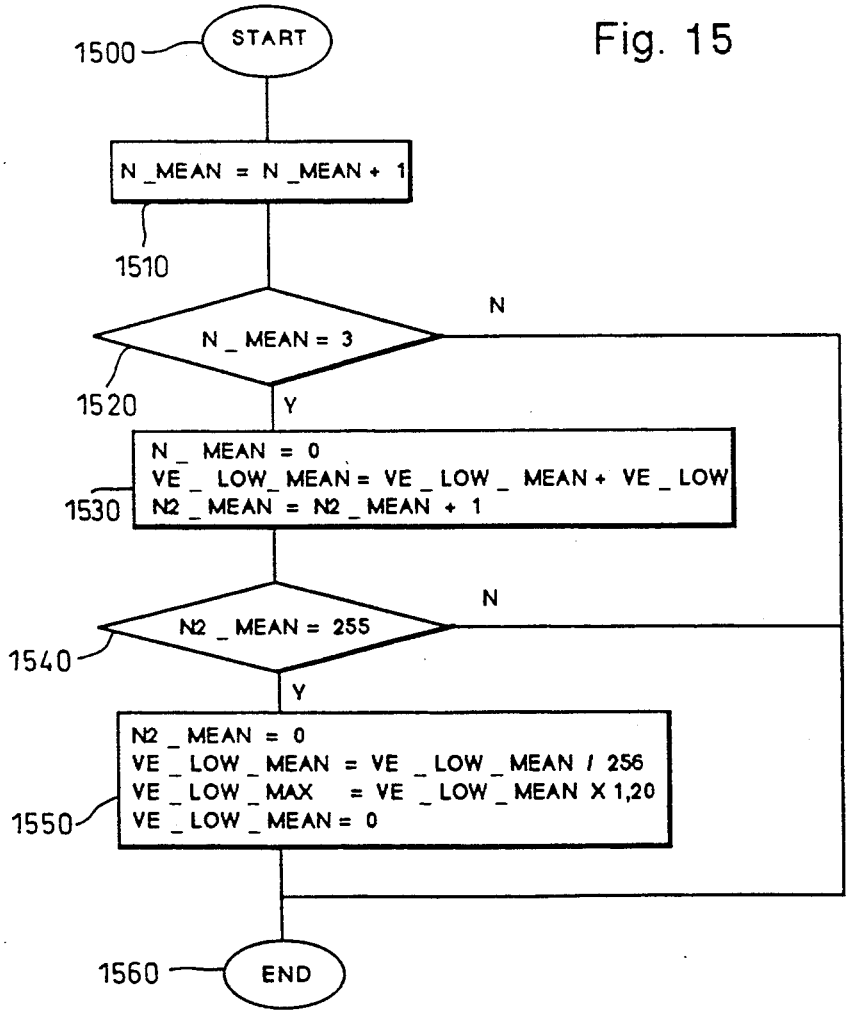
FIG. 15 is a logical diagram for the Calculation Limit VE low/mean in accordance with an embodiment of the present invention.

Referring to FIG. 15, the Routine CALCULATE VE LOW/MEAN is entered at 1500 and proceeds to box 1510 where a counter N_Mean is incremented and then to box 1520 where counter N_Mean is queried to determine whether it is equal to 3. If it is not, then the routine passes to exit at 1560. If it is, that means that the routine CALCULATE VE LOW/MEAN has been accessed four times corresponding to the passage of 32 breathing cycles and certain parameters need to be updated. In this case, the routine passes box 1530 where the counter N_Mean is reset to 0, the term VE low/mean is set equal to VE low/mean plus VE low, and the counter N2_Mean is incremented by 1. The routine then passes to box 1540 where counter N2_Mean is queried to determine whether it is equal to 255. If it is not, then the routine exits at 1560. If it is, then the routine passes to box 1550 and the term VE low/mean is recalculated. In this regard, counter N2_Mean is reset to 0. The term VE low/mean is set equal to VE low/mean divided by 256, the term VE low/max is set equal to VE low/mean times 1.2, and the term VE low/mean is reset to zero. Thus, the value of VE low/max is updated. Thereafter, the routine exits at 1560.

It should be understood that the invention is applicable to any control function relating a physiological parameter representative of the activity of the patient other than minute volume, including without limitation, linear functions such as the breathing rate or the pre-ejection period, to the cardiac pacing rate.

The method of the invention is preferably performed by a computer, more preferably, an eight bit microprocessor device having software instructions in an associated memory device, an input for receiving the calculated cardiac rate based on a selected control relationship, an input of the measure of the physiological parameter, e.g., minute volume, and an output for providing the selected pacing rate. A preferred device is the microprocessor of a rate adaptive metabolic demand dual chamber pacemaker having input parameters programmable for the patient's characteristics in the known manner. Appropriate devices for converting analog circuit signals to digital signals and vice versa may be provided. It is to be understood, however, that the method also may be performed by analog circuit devices, and by a combination of digital and analog circuits. All of the foregoing components are conventional.

A suitable microprocessor controlled dual chamber pacemaker for use with the present invention is the one used in the model CHORUS I or II, available from Ela Medical, Montrouge, France, provided that it is first modified with a sensor, circuits and signal processing algorithm to acquire the measure of minute volume and provided with a suitable algorithm to calculate a pacing rate in response to the minute volume.

A preferred embodiment of a software program useful for controlling a microprocessor controlled metabolic demand dual-chambered pacemaker in accordance with the present invention is set forth in the software appendix and is expressed in the program description language following.

The term "temp vent 32" refers to VE/32; the term "Resp counter" refers to counter C2, the term "Sensor fallback State" refers to authorization to use rate responsive mode on; the term "cycle count no calc 1" refers to the counter C1; the term "vent 1" refers to a measure of minute volume VE during a breathing cycle; the terms "Temp" and "Temp1" refers to temporary parameters used in the calculations; the term "Percent MVV" refers to the programmed value Y; the term "cycle no calc 2" refers to a counter for determining if eight breathing cycles have occurred; the term "max vent calib" corresponds to VE max; the term "max volunt vent" refers to MVV; the term "Exercise state" refers to the patient's level of activity being at rest or not at rest; the term "Aver vent 8-0" refers to mean VE/8 and "Vent 4 Stack" is the stack memory for holding 4 measures VE for use in forming VE/8; the terms "TEMP Vent 32," "Aver Vent 64" and "Last Vent 32" are parameters used to calculate "Aver Vent 64", which is VE/64 using the last two averages of 32 measures of VE; the term "min vent calib max" refers to the minimum level for VE max; the term "min vent calib" refers to VE low; the term "min vent calib max" refers to upper limit for VE low; and the term "min vent calib aver" refers to the term VE low/mean.

Routine MIN & MAX VENT CALC
PROC
    "Temp vent 32" = "temp vent 32" + "Ventil"
    IF "Resp counter" modulo 8 = 7
    THEN
        Max vent calc
        IF "Resp counter" = 31

-continued
    THEN
        IF "Sensor fallback state" = ASSES
        THEN
            Min vent calc
        ELSE
            "Cycle count no calc 1" = 0
        FI
        "Temp vent 32" = 0
        Calc "Min vent calib aver"
    ELSE
        Rien
    FI
ELSE
    Rien
FI
CORP Routine MAX VENT CALC
"Temp" = "Min vent calib" * "Per cent mvv"
IF
    "Cycle count no calc 2" < 3072
THEN
    "Cycle count no calc 2" = "Cycle count no calc 2" + 1
    IF
        "Max vent calib" < "Max volunt vent"
    THEN
        IF   OR
            "Exercise state" < > rest
            "Prg SAFA" = 0
            RO
        THEN
    "Aver vent 8−0" =
        1
        (Σ Vent 4 stack ("Vent 4 ptr"
        i=0                      −2+i modulo 4))/2
        IF
            "Aver vent 8−0" > "Max vent calib"
        THEN
            "Temp1" = "Max vent calib" *
            (1 + 0.06)
            IF
                "Temp1" > "Aver vent 8−0"
            THEN
                "Max vent calib" = "Aver vent 8−0"
            ELSE
                "Max vent calib" = "Temp1"
            FI
            Max vent calib limit
            "Flag calib2" = 1
            add 1 to "stat for max vent calib"
            "Cycle count no calc 2" = 0
        ELSE
            rien
        FI
    ELSE
    FI
ELSE
FI
ELSE
    If "Max vent calib" > "Temp"
    THEN
        "Max vent calib" = "Max vent calib" * (1 − 0.03)
        Max vent calib limit
        "Flag calib2" = 1
        add 1 to "stat for max vent calib"
        "Cycle count no calc 2" = 0
    ELSE
    FI
FI Routine MIN VENT CALC
"Temp vent 32" = "Temp vent 32"/8
"Aver vent 64" = ("Temp vent 32" + "Last vent 32")/2
"Last vent 32" = "Temp vent 32"
CASE ("Aver vent 64")
PART ( < "Min vent calib" * (1 − 0.06) )
    "Min vent calib" = "Min vent calib"*(1−0.06)
    Calc max volunt vent
    Max vent calib limit
    "Flag calib1" = 1
    add 1 to "stat for min vent calib"

-continued
```
"Cycle count no calc 1" = 0
PART ( > "Min vent calib" * (1 + 0.06) )
IF
    "Min vent calib" < "Min vent calib max"
THEN
    IF
        "Cycle count no calc 1" = 8
    THEN
        "Min vent calib" = "Min vent calib" *
            (1 + 0.06)
        Min vent calib limit
        Calc max volunt vent
        Max vent calib limit
        "Flag calib1" = 1
        add 1 to "stat for min vent calib"
        "Cycle count no calc 1" = 0
    ELSE
        "Cycle count no calc 1" = "Cycle
            count no calc1" + 1
    FI
ELSE
FI
ELSE
ESAC
```

Routine CALC MAX VOLUNT VENT
```
IF
    "Max vent calib" = "Temp"
THEN
    "Max vent calib" = "Min vent calib" * "Per cent MVV"
ELSE
    rien
FI
"Max volunt vent " = "Min vent calib" * 16
"Temp" = "Min vent calib" * "Per cent mvv"
IF "Max volunt vent" > FFFFH
THEN
    Max volunt vent" = FFFFH
ELSE
FI
```

Routine MAX VENT CALIB LIMIT
```
IF
    "Max vent calib" > "Max volunt vent"
THEN
    "Max vent calib" = "Max volunt vent"
ELSE
    IF
        "Max vent calib" < "Temp"
    THEN
        "Max vent calib" = "Temp"
        add 1 to "stat for max vent calib min"
    ELSE
        rien
    FI
FI
```

Routine MIN VENT CALIB LIMIT
```
IF
    "Min vent calib" > "Min vent calib max"
THEN
    "Min vent calib" = "Min vent calib max"
    add 1 to "stat for min vent calib max"
ELSE
FI
```

Routine CALC "MIN VENT CALIB AVER"
```
IF
    "Counter 96" = 2
THEN
    "Counter 96" = 0
    "Min vent calib aver" = "Min vent calib aver" +
        "Min vent calib"
    IF
        "Counter aver" = 255
    THEN
        "Counter aver" = 0
        "Min vent calib aver" = "Min vent calib aver"/256
        "Min vent calib max" = "Min vent calib aver" *
            (1 + "Percent aver")
        "Min vent calib aver" = 0
    ELSE
    FI
ELSE
    "Counter 96" = "Counter 96" + 1
FI
```

Preparation of alternate suitable software for controlling other metabolic demand microprocessor controlled pacemakers, to operate in accordance with the present invention is believed to be well within the ability of a person of ordinary skill in the art.

One skilled in the art will appreciate that the present invention can be practiced by other than the described embodiments which are presented for purposes of illustration and not of limitation.

```
3283        ;
3284        ;
3285        ;       ******************************
3286        ;       *    MIN & MAX VENTIL CALC   *
3287        ;       ******************************
3288        ;
3289        ;
3290  F2E2  A5 BF   MAXCYCNC2:  LDA   MAXVENCAL
3291  F2E4  A6 C0               LDX   MAXVENCAL+1
3292  F2E6  E4 8A               CPX   TEMP2
3293  F2E8  F0 04               BEQ   COMPTEMP1
3294  F2EA  B0 08               BCS   CALCMXVC
3295  F2EC  80 1D               BRA   MINVENC
3296  F2EE  C5 89   COMPTEMP1:  CMP   TEMP1
3297  F2F0  F0 19               BEQ   MINVENC
3298  F2F2  90 17               BCC   MINVENC
3299  F2F4  85 8B   CALCMXVC:   STA   TEMP3
3300  F2F6  8A                  TXA
3301  F2F7  A0 05               LDY   #5
3302  F2F9  20 46 F5            JSR   CALCPC003
3303  F2FC  A5 BF               LDA   MAXVENCAL
3304  F2FE  38                  SEC
3305  F2FF  E5 8B               SBC   TEMP3
3306  F301  85 BF               STA   MAXVENCAL
3307  F303  8A                  TXA
3308  F304  E5 8C               SBC   TEMP4
```

© 1991 Ela Medical
This is a portion of an unpublished work: CHORUS II CODE max vent calib*(1_0.03)

| | | | | | | |
|---|---|---|---|---|---|---|
| 3309 | F306 | 85 C0 | | STA | MAXVENCAL+1 | |
| 3310 | F308 | 4C A0 F3 | | JMP | MAXVCLIM | |
| 3311 | | | ; | | | |
| 3312 | F30B | 20 B4 F3 | MINVENC: | JSR | MINCALC | |
| 3313 | F30E | 60 | ENDMMXCAL: | RTS | | |
| 3314 | | | ; | | | |
| 3315 | F30F | A5 67 | MMXVCALC: | LDA | PCALIB | |
| 3316 | F311 | F0 FB | | BEQ | ENDMMXCAL | |
| 3317 | F313 | A5 D5 | | LDA | VENTIL | |
| 3318 | F315 | 18 | | CLC | | |
| 3319 | F316 | 6D 3F 01 | | ADC | TVEN32 | |
| 3320 | F319 | 8D 3F 01 | | STA | TVEN32 | |
| 3321 | F31C | A5 D6 | | LDA | VENTIL+1 | ;temp vent 32=temp vent 32+ ventil |
| 3322 | F31E | 6D 40 01 | | ADC | TVEN32+1 | |
| 3323 | F321 | 8D 40 01 | | STA | TVEN32+1 | |
| 3324 | F324 | 90 03 | | BCC | MAXVENC12 | |
| 3325 | F326 | EE 41 01 | | INC | TVEN32+2 | |
| 3326 | F329 | A5 E2 | MAXVENC12: | LDA | RESPCNT | |
| 3327 | F32B | 29 07 | | AND | £7 | resp counter modulo 8 |
| 3328 | F32D | C9 07 | | CMP | £7 | |
| 3329 | F32F | D0 DD | | BNE | ENDMMXCAL | resp counter modulo 8 <> 7 |
| 3330 | F331 | 20 AC F5 | | JSR | MULTMINVC | min vent calib * pc |
| 3331 | F334 | A5 FD | | LDA | CYCOUNTNC2+1 | |
| 3332 | F336 | C9 0C | | CMP | £0CH | |
| 3333 | F338 | B0 A8 | | BCS | MAXCYCNC2 | cycle count no calc 2=3072 |
| 3334 | F33A | E6 FC | INFMAX1: | INC | CYCOUNTNC2 | |
| 3335 | F33C | D0 02 | | BNE | INFMAX2 | |
| 3336 | F33E | E6 FD | | INC | CYCOUNTNC2+1 | |
| 3337 | F340 | A5 C0 | INFMAX2: | LDA | MAXVENCAL+1 | |
| 3338 | F342 | C5 C2 | | CMP | MVV+1 | |
| 3339 | F344 | F0 04 | | BEQ | MAXVENC1 | max vent calib+1=max volunt vent+1 |
| 3173 | F22B | 80 06 | | BRA | SETSENS | |
| 3174 | F22D | C5 46 | UPDSENS1: | CMP | PBASPER | |
| 3175 | F22F | 90 02 | | BCC | SETSENS | A < prg bas per |
| 3176 | F231 | A5 46 | | LDA | PBASPER | |
| 3177 | F233 | 85 E7 | SETSENS: | STA | SENSESCPER | sensor esc per = A |
| 3178 | F235 | 60 | | RTS | | |
| 3179 | | | ; | | | |
| 3180 | F236 | C4 E7 | EXER: | CPY | SENSESCPER | |
| 3181 | F238 | F0 CB | | BEQ | CALCSENS | ; present cycle per <= |
| 3182 | F23A | 90 C9 | | BCC | CALCSENS | ; sensor esc per |
| 3183 | F23C | 64 89 | | STZ | TEMP1 | |
| 3184 | F23E | A6 E1 | | LDX | VENT4PTR | |
| 3185 | F240 | 20 84 F2 | | JSR | CALCAVER8 | |
| 3186 | F243 | 85 F6 | | STA | AVERVEN81+1 | |
| 3187 | F245 | 90 02 | | BCC | SETAVER8 | |
| 3188 | F247 | E6 89 | | INC | TEMP1 | |
| 3189 | F249 | A5 8B | SETAVER8: | LDA | TEMP3 | |
| 3190 | F24B | 85 F5 | | STA | AVERVEN81 | |
| 3191 | F24D | E8 | | INX | | |
| 3192 | F24E | E0 08 | | CPX | £8 | |
| 3193 | F250 | D0 02 | | BNE | EXER2 | |
| 3194 | F252 | A2 00 | | LDX | £0 | |
| 3195 | F254 | 20 84 F2 | EXER2: | JSR | CALCAVER8 | |
| 3196 | F257 | A0 00 | | LDY | £0 | |
| 3197 | F259 | A6 8B | | LDX | TEMP3 | |
| 3198 | F25B | 86 B5 | | STX | AVERVEN80 | |
| 3199 | F25D | 85 B6 | | STA | AVERVEN80+1 | |
| 3200 | F25F | 90 05 | | BCC | COMP1 | |
| 3201 | F261 | C4 89 | | CPY | TEMP1 | |
| 3202 | F263 | D0 07 | | BNE | COMP2 | |
| 3203 | F265 | 60 | | RTS | | |
| 3204 | | | ; | | | |
| 3205 | F266 | C4 89 | COMP1: | CPY | TEMP1 | |
| 3206 | F268 | F0 02 | | BEQ | COMP2 | |
| 3207 | F26A | 80 11 | | BRA | INF | |
| 3208 | | | ; | | | |
| 3209 | F26C | A5 B6 | COMP2: | LDA | AVERVEN80+1 | compare aver ven 80+1 et aver 81+1 |
| 3210 | F26E | C5 F6 | | CMP | AVERVEN81+1 | |
| 3211 | F270 | F0 03 | | BEQ | COMP3 | aver ven 80+1=aver ven 81+1 |
| 3212 | F272 | 90 09 | | BCC | INF | aver ven 80+1<aver ven 81+1 |

| | | | | | | |
|---|---|---|---|---|---|---|
| 3213 | F274 | 60 | FINEXER: | RTS | | |
| 3214 | F275 | A5 B5 | COMP3: | LDA | AVERVEN80 | |
| 3215 | F277 | C5 F5 | | CMP | AVERVEN81 | |
| 3216 | F279 | F0 02 | | BEQ | INF | |
| 3217 | F27B | B0 F7 | | BCS | FINEXER | ;Aver ven 80>aver ven 81 |
| 3218 | F27D | E6 BC | INF: | INC | EXERCISE | exercise = reco |
| 3219 | F27F | A4 C8 | | LDY | PRESCYPER | |
| 3220 | F281 | 4C 00 F2 | | JMP | RECO1 | |
| 3221 | | | ; | | | |
| 3222 | | | | PAGE | | |
| 3340 | F346 | 90 08 | | BCC | TESTEXER | max vent calib+1<ma unt vent+1 |
| 3341 | F348 | 80 C1 | | BRA | MINVENC | |
| 3342 | F34A | A5 BF | MAXVENC1: | LDA | MAXVENCAL | |
| 3343 | F34C | C5 C1 | | CMP | MVV | |
| 3344 | F34E | B0 BB | | BCS | MINVENC | max vent calib>=max volunt vent |
| 3345 | F350 | A5 BC | TESTEXER: | LDA | EXERCISE | |
| 3346 | F352 | D0 04 | | BNE | AVER8CALC | exercise state <> 0 |
| 3347 | F354 | A5 68 | | LDA | PSAFA | |
| 3348 | F356 | D0 B3 | | BNE | MINVENC | prg safa <> 0 |
| 3349 | F358 | A5 E1 | AVER8CALC: | LDA | VENT4PTR | calcul de aver vent 80 |
| 3350 | F35A | 18 | | CLC | | |
| 3351 | F35B | 69 04 | | ADC | £4 | |
| 3352 | F35D | 29 07 | | AND | £7 | modulo 7 |
| 3353 | F35F | AA | | TAX | | |
| 3354 | F360 | 20 84 F2 | | JSR | CALCAVER8 | |
| 3355 | F363 | 6A | | ROR | A | |
| 3356 | F364 | 85 B6 | | STA | AVERVEN80+1 | |
| 3357 | F366 | A5 8B | | LDA | TEMP3 | |
| 3358 | F368 | 6A | | ROR | A | |
| 3359 | F369 | 85 B5 | | STA | AVERVEN80 | |
| 3360 | F36B | A6 C0 | | LDX | MAXVENCAL+1 | |
| 3361 | F36D | E4 B6 | | CPX | AVERVEN80+1 | |
| 3362 | F36F | F0 04 | | BEQ | MAXVENC3 | max vent calib+1=aver vent 80+1 |
| 3363 | F371 | 90 08 | | BCC | PCMAXVC | max vent calib+1>aver vent 80+1 |
| 3364 | F373 | 80 3F | | BRA | MINCALC | |
| 3365 | F375 | A5 BF | MAXVENC3: | LDA | MAXVENCAL | |
| 3366 | F377 | C5 B5 | | CMP | AVERVEN80 | |
| 3367 | F379 | B0 39 | | BCS | MINCALC | |
| 3368 | F37B | A5 BF | PCMAXVC: | LDA | MAXVENCAL | ; |
| 3369 | F37D | 85 8B | | STA | TEMP3 | max vent calib*(1+2*0.03) |
| 3370 | F37F | 8A | | TXA | | |
| 3371 | F380 | 20 44 F5 | | JSR | CALCPC006 | |
| 3372 | F383 | A5 BF | | LDA | MAXVENCAL | |
| 3373 | F385 | 18 | | CLC | | ; (1+2*per cent 2) |
| 3374 | F386 | 65 8B | | ADC | TEMP3 | ; |
| 3375 | F388 | A8 | | TAY | | ; |
| 3376 | F389 | 8A | | TXA | | ; |
| 3377 | F38A | 65 8C | | ADC | TEMP4 | ; |
| 3378 | F38C | C5 B6 | | CMP | AVERVEN80+1 | |
| 3379 | F38E | F0 04 | | BEQ | COMPAVER | aver vent 80+1=max vent calib*1.06 |
| 3380 | F390 | 90 0A | | BCC | MAXVENC4 | |
| 3381 | F392 | 80 04 | | BRA | SETAVER80 | |
| 3382 | F394 | C4 B5 | COMPAVER: | CPY | AVERVEN80 | |
| 3383 | F396 | 90 04 | | BCC | MAXVENC4 | |
| 3384 | F398 | A4 B5 | SETAVER80: | LDY | AVERVEN80 | |
| 3385 | F39A | A5 B6 | | LDA | AVERVEN80+1 | |
| 3386 | F39C | 84 BF | MAXVENC4: | STY | MAXVENCAL | |
| 3387 | F39E | 85 C0 | | STA | MAXVENCAL+1 | |
| 3388 | F3A0 | A9 01 | MAXVCLIM: | LDA | £1 | |
| 3389 | F3A2 | 8D 46 01 | | STA | FCALIB2 | flag calib 2 = 1 |
| 3390 | F3A5 | 64 FC | | STZ | CYCOUNTNC2 | |
| 3391 | F3A7 | 64 FD | | STZ | CYCOUNTNC2+1 | |
| 3392 | F3A9 | EE E4 01 | | INC | STMAXVENC | |
| 3393 | F3AC | D0 03 | | BNE | MAXVCLIM1 | |
| 3394 | | | ; | INC | STMAXVENC+1 | |
| 3395 | | | ; | BNE | MAXVCLIM1 | |
| 3396 | | | ; | DEC | STMAXVENC+1 | |
| 3397 | F3AE | CE E4 01 | | DEC | STMAXVENC | |
| 3398 | F3B1 | 20 DF F4 | MAXVCLIM1: | JSR | MAXVCLIM2 | |
| 3399 | | | ; | | | |
| 3400 | F3B4 | A5 E2 | MINCALC: | LDA | RESPCNT | |

| | | | | | |
|---|---|---|---|---|---|
| 3401 | F3B6 | C9 1F | | CMP | £31 |
| 3402 | F3B8 | D0 6A | | BNE | NOTEQ31 | resp counter<>31 |
| 3403 | F3BA | A5 E6 | | LDA | SENSFALLB |
| 3404 | F3BC | D0 67 | | BNE | NOTEQASS | sensor fallback state<>asses |
| 3405 | F3BE | AD 3F 01 | | LDA | TVEN32 |
| 3406 | F3C1 | A2 03 | | LDX | £3 |
| 3407 | F3C3 | 4E 41 01 | CALCV32: | LSR | TVEN32+2 |
| 3408 | F3C6 | 6E 40 01 | | ROR | TVEN32+1 | ; temp vent 32 = |
| 3409 | F3C9 | 6A | | ROR | A | ; temp vent 32/8 |
| 3410 | F3CA | CA | | DEX |
| 3411 | F3CB | D0 F6 | | BNE | CALCV32 |
| 3412 | F3CD | AA | | TAX |
| 3413 | F3CE | 18 | | CLC |
| 3414 | F3CF | 6D 0A 01 | | ADC | LASTVEN32 |
| 3415 | F3D2 | 85 F7 | | STA | AVERVEN64 |
| 3416 | F3D4 | AD 40 01 | | LDA | TVEN32+1 | ; aver vent 64=(temp vent 32+ |
| 3417 | F3D7 | 6D 0B 01 | | ADC | LASTVEN32+1 | ;        last vent 32)/2 |
| 3418 | F3DA | 6A | | ROR | A |
| 3419 | F3DB | 85 F8 | | STA | AVERVEN64+1 |
| 3420 | F3DD | 66 F7 | | ROR | AVERVEN64 |
| 3421 | F3DF | 8E 0A 01 | | STX | LASTVEN32 |
| 3422 | F3E2 | AD 40 01 | | LDA | TVEN32+1 | ; last vent 32=temp vent 32 |
| 3423 | F3E5 | 8D 0B 01 | | STA | LASTVEN32+1 |
| 3424 | F3E8 | A6 C4 | | LDX | MINVENCAL |
| 3425 | F3EA | 86 8B | | STX | TEMP3 |
| 3426 | F3EC | A5 C5 | | LDA | MINVENCAL+1 |
| 3427 | F3EE | 20 44 F5 | | JSR | CALCPC006 | min vent calib*0.06 |
| 3428 | F3F1 | 8A | | TXA |
| 3429 | F3F2 | 38 | | SEC |
| 3430 | F3F3 | E5 8B | | SBC | TEMP3 | ; min vent calib*(1-0.06) |
| 3431 | F3F5 | AA | | TAX | | ; dans X et A |
| 3432 | F3F6 | A5 C5 | | LDA | MINVENCAL+1 |
| 3433 | F3F8 | E5 8C | | SBC | TEMP4 |
| 3434 | F3FA | C5 F8 | | CMP | AVERVEN64+1 |
| 3435 | F3FC | F0 04 | | BEQ | COMP031 |
| 3436 | F3FE | 90 29 | | BCC | MINVENC2 | aver vent 64>=min vent calib*(1-0.06) |
| 3437 | F400 | 80 06 | | BRA | CALCMVV |
| 3438 | F402 | E4 F7 | COMP031: | CPX | AVERVEN64 |
| 3439 | F404 | F0 23 | | BEQ | MINVENC2 | aver vent 64=min vent calib*(1-0.06) |
| 3440 | F406 | 90 21 | | BCC | MINVENC2 | aver vent 64>min vent calib*(1-0.06) |
| 3441 | F408 | 86 C4 | CALCMVV: | STX | MINVENCAL | ; min vent calib= |
| 3442 | F40A | 85 C5 | | STA | MINVENCAL+1 | ; min vent calib*(1-0.06) |
| 3443 | F40C | A9 01 | | LDA | £1 |
| 3444 | F40E | 8D 45 01 | | STA | FCALIB1  flag calib 1 = 1 |
| 3445 | F411 | 64 FB | | STZ | CYCOUNTNC1 |
| 3446 | F413 | EE E3 01 | | INC | STMINVENC |
| 3447 | F416 | D0 03 | | BNE | MVVCALC |
| 3448 | | | ; | INC | STMINVENC+1 |
| 3449 | | | ; | BNE | MVVCALC |
| 3450 | | | ; | DEC | STMINVENC+1 |
| 3451 | F418 | CE E3 01 | | DEC | STMINVENC |
| 3452 | | | ; |
| 3453 | F41B | 20 0E F5 | MVVCALC: | JSR | CMAXVOLVEN |
| 3454 | F41E | 20 DF F4 | ENDMXVV: | JSR | MAXVCLIM2 |
| 3455 | F421 | 4C 73 F4 | | JMP | MINCALEND |
| 3456 | | | ; |
| 3457 | F424 | 60 | NOTEQ31: | RTS |
| 3458 | | | ; |
| 3459 | F425 | 64 FB | NOTEQASS: | STZ | CYCOUNTNC1 |
| 3460 | F427 | 80 4A | | BRA | MINCALEND |
| 3461 | | | ; |
| 3462 | F429 | A5 C4 | MINVENC2: | LDA | MINVENCAL |
| 3463 | F42B | 18 | | CLC |
| 3464 | F42C | 65 8B | | ADC | TEMP3 | ; min vent calib*(1+0.06) |
| 3465 | F42E | AA | | TAX | | ; dans X et A |
| 3466 | F42F | A5 C5 | | LDA | MINVENCAL+1 |
| 3467 | F431 | A8 | | TAY |
| 3468 | F432 | 65 8C | | ADC | TEMP4 |
| 3469 | F434 | C5 F8 | | CMP | AVERVEN64+1 |
| 3470 | F436 | F0 04 | | BEQ | PARTSUP |
| 3471 | F438 | B0 39 | | BCS | MINCALEND |

| | | | | | | |
|---|---|---|---|---|---|---|
|3472|F43A|80 04| |BRA|ADD003| |
|3473|F43C|E4 F7|PARTSUP:|CPX|AVERVEN64| |
|3474|F43E|B0 33| |BCS|MINCALEND| |
|3475|F440|C4 C7|ADD003:|CPY|MINVCALMX+1| |
|3476|F442|F0 04| |BEQ|CMINVCMX| |
|3477|F444|90 08| |BCC|COMPCYC1| |
|3478|F446|80 2B| |BRA|MINCALEND| |
|3479|F448|A4 C4|CMINVCMX:|LDY|MINVENCAL| |
|3480|F44A|C4 C6| |CPY|MINVCALMX| |
|3481|F44C|B0 25| |BCS|MINCALEND| |
|3482|F44E|A4 FB|COMPCYC1:|LDY|CYCOUNTMC1| |
|3483|F450|C0 08| |CPY|£8| |
|3484|F452|D0 1D| |BNE|INCCNTMC1| |
|3485|F454|C5 C7| |CMP|MINVCALMX+1| |
|3486|F456|F0 04| |BEQ|COMPMAX| |
|3487|F458|B0 08| |BCS|SETMAX| |
|3488|F45A|80 12| |BRA|ENDMINVC2| |
|3489|F45C|E4 C6|COMPMAX:|CPX|MINVCALMX| |
|3490|F45E|F0 0E| |BEQ|ENDMINVC2| |
|3491|F460|90 0C| |BCC|ENDMINVC2| |
|3492|F462|A5 C7|SETMAX:|LDA|MINVCALMX+1| |
|3493|F464|A6 C6| |LDX|MINVCALMX| |
|3494|F466|EE E1 01| |INC|STMINVCH| |
|3495|F469|D0 03| |BNE|ENDMINVC2| |
|3496|F46B|CE E1 01| |DEC|STMINVCH| |
|3497|F46E|4C 08 F4|ENDMINVC2:|JMP|CALCMVV| |
|3498| | |;| | | |
|3499|F471|E6 FB|INCCNTMC1:|INC|CYCOUNTMC1| |
|3500|F473|9C 3F 01|MINCALEND:|STZ|TVEN32| |
|3501|F476|9C 40 01| |STZ|TVEN32+1| |
|3502|F479|9C 41 01| |STZ|TVEN32+2| |
|3503| | |;|JSR|TCALIB| |
|3504|F47C|A5 F9| |LDA|COUNT96| |
|3505|F47E|C9 02| |CMP|£2| |
|3506|F480|D0 5A| |BNE|INCOUNT96|counter 96 <> 2|
|3507|F482|64 F9| |STZ|COUNT96| |
|3508|F484|A5 C4| |LDA|MINVENCAL| |
|3509|F486|18| |CLC| | |
|3510|F487|6D 02 01| |ADC|MINVCALAV|min vent calib aver=|
|3511|F48A|8D 02 01| |STA|MINVCALAV|min vent cali : +|
|3512|F48D|A5 C5| |LDA|MINVENCAL+1|min vent calib|
|3513|F48F|6D 03 01| |ADC|MINVCALAV+1| |
|3514|F492|8D 03 01| |STA|MINVCALAV+1| |
|3515|F495|90 03| |BCC|CALCMVCAV| |
|3516|F497|EE 04 01| |INC|MINVCALAV+2| |
|3517|F49A|E6 FA|CALCMVCAV:|INC|COUNTAVER| |
|3518|F49C|A6 FA| |LDX|COUNTAVER| |
|3519|F49E|E0 FF| |CPX|£255| |
|3520|F4A0|D0 39| |BNE|ENDMIVCAV|counter aver <> 255|
|3521|F4A2|64 FA| |STZ|COUNTAVER| |
|3522|F4A4|AE 04 01| |LDX|MINVCALAV+2| |
|3523|F4A7|85 8B|CALCPC20:|STA|TEMP3| |
|3524|F4A9|86 8C| |STX|TEMP4| |
|3525|F4AB|86 8A| |STX|TEMP2| |
|3526|F4AD|9C 02 01| |STZ|MINVCALAV| |
|3527|F4B0|9C 03 01| |STZ|MINVCALAV+1| |
|3528|F4B3|9C 04 01| |STZ|MINVCALAV+2| |
|3529|F4B6|46 8A|CALCPC201:|LSR|TEMP2| |
|3530|F4B8|6A| |ROR|A| |
|3531|F4B9|46 8A| |LSR|TEMP2|min vent calib aver*0.20|
|3532|F4BB|6A| |ROR|A|dans TEMP1 et TEMP2|
|3533|F4BC|A8| |TAY| | |
|3534|F4BD|A6 8A| |LDX|TEMP2| |
|3535|F4BF|46 8A| |LSR|TEMP2| |
|3536|F4C1|6A| |ROR|A| |
|3537|F4C2|46 8A| |LSR|TEMP2| |
|3538|F4C4|6A| |ROR|A| |
|3539|F4C5|85 89| |STA|TEMP1| |
|3540|F4C7|98| |TYA| | |
|3541|F4C8|38| |SEC| | |
|3542|F4C9|E5 89| |SBC|TEMP1| |

```
3543  F4CB  A8                 TAY
3544  F4CC  8A                 TXA
3545  F4CD  E5 8A              SBC   TEMP2
3546  F4CF  AA                 TAX
3547  F4D0  98                 TYA
3548  F4D1  18                 CLC                      ; min vent calib max=
3549  F4D2  65 8B              ADC   TEMP3              ; min vent calib aver*(1+0.25)
3550  F4D4  85 C6              STA   MINVCALMX
3551  F4D6  8A                 TXA
3552  F4D7  65 8C              ADC   TEMP4
3553  F4D9  85 C7              STA   MINVCALMX+1
3554  F4DB  60    ENDMIVCAV:   RTS
3555  F4DC  E6 F9 INCOUNT96:   INC   COUNT96
3556  F4DE  60                 RTS
3557                    ;
3558                    ;
3559                    ;
3560                    ;     **************************
3561                    ;     *   MAX VENT CALIB LIMIT  *
3562                    ;     **************************
3563                    ;
3564  F4DF  A5 C1 MAXVCLIM2:   LDA   MVV
3565  F4E1  A6 C2              LDX   MVV+1
3566  F4E3  E4 C0              CPX   MAXVENCAL+1
3567  F4E5  F0 04              BEQ   COMPMVV
3568  F4E7  B0 08              BCS   COMPMAXVC1         max volunt vent+.   . vent calib+1
3569  F4E9  80 1E              BRA   SETMXVCAL
3570  F4EB  C5 BF COMPMVV:     CMP   MAXVENCAL
3571  F4ED  F0 02              BEQ   COMPMAXVC1
3572  F4EF  B0 18              BCS   SETMXVCAL          max volunt vent<max vent calib
3573  F4F1  A6 3A COMPMAXVC1:  LDX   TEMP2
3574  F4F3  A5 89              LDA   TEMP1
3575  F4F5  E4 C0              CPX   MAXVENCAL+1
3576  F4F7  F0 04              BEQ   COMPMAXVC2
3577  F4F9  90 12              BCC   ENDCMVV
3578  F4FB  80 04              BRA   SETMXVCEL
3579  F4FD  C5 BF COMPMAXVC2:  CMP   MAXVENCAL
3580  F4FF  90 0C              BCC   ENDCMVV
3581  F501  EE E2 01 SETMXVCEL:INC   STMAXVCM
3582  F504  D0 03              BNE   SETMXVCAL
3583  F506  CE E2 01           DEC   STMAXVCM
3584  F509  85 BF SETMXVCAL:   STA   MAXVENCAL
3585  F50B  86 C0              STX   MAXVENCAL+1
3586  F50D  60    ENDCMVV:     RTS
3587                    ;
3588                    ;     **************************
3589                    ;     *   CALC MAX VOLUNT VENT *
3590                    ;     **************************
3591                    ;
3592  F50E  A5 BF CMAXVOLVEN:  LDA   MAXVENCAL          fct CALC MAX VOLUNT VENT
3593  F510  C5 89              CMP   TEMP1
3594  F512  D0 13              BNE   ENDCOMP            max vent calib<>temp
3595  F514  A5 C0              LDA   MAXVENCAL+1
3596  F516  C5 8A              CMP   TEMP2
3597  F518  D0 0D              BNE   ENDCOMP            max vent calib<>temp
3598  F51A  20 AC F5           JSR   MULTMINVC
3599  F51D  A5 89              LDA   TEMP1
3600  F51F  85 BF              STA   MAXVENCAL          ; max vent calib =
3601  F521  A5 8A              LDA   TEMP2              ; min vent calib*pc
3602  F523  85 C0              STA   MAXVENCAL+1
3603  F525  80 03              BRA   SETMVV
3604  F527  20 AC F5 ENDCOMP:  JSR   MULTMINVC
3605  F52A  A5 C4 SETMVV:      LDA   MINVENCAL
3606  F52C  85 C1              STA   MVV
3607  F52E  A5 C5              LDA   MINVENCAL+1
3608  F530  A2 04              LDX   #4
3609  F532  06 C1 BCLCALMVV:   ASL   MVV
3610  F534  2A                 ROL   A                  ; max volunt vent =
3611  F535  B0 06              BCS   SETFFFF
```

```
3612  F537  CA              DEX
3613  F538  D0 F8            BNE   BCLCALMVV
3614  F53A  85 C2            STA   MVV+1
3615  F53C  60               RTS
3616                  ;
3617  F53D  A9 FF    SETFFFF: LDA   #FFH
3618  F53F  85 C1            STA   MVV
3619  F541  85 C2            STA   MVV+1
3620  F543  60               RTS
3621                  ;
3622                  ;
3623                  ;***************
3624                  ;  * CALCPC006 *
```

We claim:

1. A method for controlling a pacemaker having a control relation between the pacing rate (FC) and a monitored physiological parameter (X) of the patient, the control relation having coefficients defining the control relation of the pacing rate having a programmed minimum rate (FC low) and a programmed maximum rate (FC max), characterized by defining a linear control relation $aX+b$, calculating automatically a value X low and a value X max corresponding to a minimum activity and a maximum activity in response to a measure of the physiological parameter, and recalculating automatically the values X low and X max in response to a second obtained measure of the physiological parameter so that the control relation is a line intersecting two pairs of values (FC low, X low) and (FC max, X max) and corresponds to the real needs of the patient.

2. A method according to claim 1, characterized in that the physiological parameter (X) is the minute volume (VE) and further characterized by initializing the control relation by calculating the minimum parameter VE low to be the mean value taken over a plurality of breathing cycles of the patient at rest, the plurality being selected from between 4 and 16, and selecting the maximum parameter VE max to be equal to a number times VE low, the number being selected from between 5 and 7.

3. A method according to claim 2, further characterized by recalculating the control relation after each modification of VE max as soon as the heart rate of the patient is less than a threshold rate defined as close to the rate FC low.

4. A method according to claim 2, further characterized by calculating every M/2 breathing cycles a mean value VE/M of the measures of VE during M preceding cycles, M being selected from between 32 and 128, and comparing the mean value VE/M to an upper limit calculated as VE low+x% and to a lower limit VE low −x%, wherein x is selected from between 3 and 9; reducing VE low by x% if VE/M is less than the lower limit, and increasing VE low by x% if VE/M is greater than the upper limit for more than a selected number of overshootings of the upper limit and VE low is not modified during those overshootings, the selected number being between 4 and 12.

5. A method according to claim 2, further characterized by calculating a limit value VE low/max as being equal to VE low/mean+y%, wherein VE low/mean is equal to the mean value of 256 values of VE low calculated every 96 breathing cycles, y being selected from between 10 and 30.

6. A method according to claim 2, further characterized by calculating the minute volume VE at each breathing cycle, calculating a mean value VE/N of the VE measures for the last N breathing cycles, N being selected from between 4 and 16, comparing the mean VE/N to the value of VE max, modifying VE max if VE/N is higher than VE max so that VE max will be equal to the smallest of the value of VE/N and Z(VE max), wherein Z is selected from between 1.03 and 1.12, and maintaining VE max the same if VE/N is less than VE max.

7. A method according to claim 6, further characterized by lowering the value of VE max on the order of 3% to 6% if the value of VE max has not been modified during a selected period on the order of 12 to 48 hours.

8. A method according to claim 6, further characterized by maintaining the modified value of VE max between an upper limit corresponding to a theoretical maximum value of the ventilation MVV calculated as a second number times VE low, the second number being greater than 10, and a lower limit corresponding to a minimum value calculated as Y(VE low), Y being selected from among the group consisting of 2, 3, 4, or 5.

9. In a pacemaker having a cardiac pacing rate that varies between a selected maximum rate and a selected minimum rate in response to a control function relating a monitored physiological parameter indicative of patient activity to a pacing rate, a method for adjusting the control function comprising:
   (a) providing a minimum activity value for the physiological parameter corresponding to patient activity;
   (b) calculating maximum activity value as a first function of the provided minimum activity value; and
   (c) calibrating the control function so that the provided minimum activity value relates to the selected minimum pacing rate and the calculated maximum activity value relates to the selected maximum pacing rate.

10. The method of claim 9 further comprising:
   (d) selecting the pacing rate in response to a measure of the physiological parameter using the calibrated control function.

11. The method of claim 10 further comprising:
modifying the maximum activity value in response to the trend of a first measure of the physiological parameter representative of maximum activity levels differing from the existing maximum activity value by more than a first threshold amount; and recalibrating the control function using the modified value maximum activity.

12. The method of claim 11 further comprising:
modifying the minimum activity value in response to the trend of a second measure of the physiological parameter representative of minimum activity levels differing from the existing minimum activity value by more than a second threshold amount; and recalibrating the control function using the modified maximum activity value.

13. The method of claim 10 further comprising, after step (d);
   (e) obtaining a first activity value based on a first time measure of the physiological parameter corresponding to the patient's average activity over a first time period;
   (f) adjusting the maximum activity value in response to the first activity value being greater than the maximum activity value, so that the adjusted maximum activity value is the lesser of the first activity value and the preexisting maximum activity value times a first constant, the first constant being selected from between 1.03 and 1.12; and
   (g) maintaining the maximum activity value unadjusted if it is greater than the first activity value.

14. A method of claim 13 wherein the physiological parameter is the minute volume and the control function is linear, providing the first function as a multiple on the order of 6 times the minimum activity level, wherein obtaining the first activity value further comprises averaging the minute volume measures obtained over the N most recent breathing cycles wherein N is selected from between 4 and 16.

15. The method of claim 13 further comprising:
   (h) recalibrating the control function in response to the adjusted maximum activity value and the pacing rate decreasing below a selected rate threshold; and thereafter
   (i) selecting the pacing rate in response to a measure of the physiological parameter using the recalibrated control function.

16. The method of claim 15 wherein step (f) further comprises adjusting the maximum activity value in response to the maximum activity value not being adjusted during a third time period, the third time period being greater than the second time period, so that the adjusted value is the preexisting maximum activity value times a second constant selected from between 0.93 and 0.97.

17. The method of claim 16 wherein the physiological parameter is the minute volume and the control function is linear, providing the first function as a multiple on the order of 6 times the minimum activity level, wherein averaging the minute volume measures obtained over the last N number of breathing cycles wherein N is selected from between 4 and 16, and the third time period is selected from between 12 and 48 hours.

18. The method of claim 16 wherein step (f) further comprising:
   providing an upper limit for the value of the maximum activity value as a second function of the minimum activity value;
   providing a lower limit for the value of the maximum activity value as a third function of the minimum activity value; and
   limiting the value of the maximum activity value to between the upper and lower limits.

19. The method of claim 18 wherein the second function is n times the minimum activity value, where n is selected to be greater than 10 and the third function is m times the minimum activity level, where m is selected from between 2 and 5.

20. The method of claim 18 further comprising;
   (j) obtaining a second activity value based on a second time measure of the physiological parameter corresponding to the patient's average activity over a second time period;
   (k) adjusting the minimum activity value in response to the second activity value being less than the minimum activity value by more than a first percent, the first percent being selected from between 3 and 9 percent, so that the adjusted value of the minimum activity level is the preceding value reduced by the selected percent; and
   (l) adjusting the minimum activity value in response to the second activity value being greater than the minimum activity value by more than a second selected percent for longer than a fourth period of time during which the minimum activity value is not adjusted, so that the adjusted value of the minimum activity value is the preceding value increased by the second percent, the second percent being selected from between 3 and 9 percent.

21. The method of claim 20 wherein step (k) further comprises:
   calculating an average of the minimum activity value values over a fifth period of time; and
   providing an upper limit for the minimum activity value as a fourth function of the calculated average minimum activity level.

22. The method of claim 20 wherein the physiological parameter is the minute volume and the control function is linear, providing the first function as a multiple on the order of 6 times the minimum activity level, wherein obtaining the first activity value further comprises averaging the minute volume measures obtained over the last N number of breathing cycles N being selected from between 4 and 16, the third time period being selected from between 12 and 48 hours, and wherein providing the second activity value further comprises calculating every M number of breathing cycles a mean value of the preceding minimum activity values during a T number of preceding breathing cycles, wherein M is selected from between 16 and 64 and T is selected from between 34 and 128.

23. The method of claim 21 wherein the fourth function is 1 times the calculated average minimum activity level, 1 being selected from between 1.1 and 1.3.

24. The method of claim 21 wherein the physiological parameter is the minute volume and the control function is linear, providing the first function as a multiple on the order of 6 times the minimum activity level, wherein obtaining the first activity value further comprises averaging the minute volume measures obtained over the last N breathing cycles, N being selected from between 4 and 16, the third time period being selected from between 12 and 48 hours, wherein obtaining the second activity value further comprises calculating every M number of breathing cycles a mean value of the preceding minimum activity values during a T number of preceding breathing cycles, wherein M is selected from between 16 and 64 and T is selected from between 34 and 128, and wherein calculating the average of the minimum activity value over the fifth period of time further comprises calculating the mean value of the minimum activity value every U number of breathing cycles, wherein U is selected from between 48 and 192.

25. The method of claim 9 wherein step (a) further comprises obtaining a first activity value based on a first time measure of the physiological parameter corresponding to the patient being in a rest activity level and, setting the minimum activity value to be the first activity value.

26. The method of claim 25 wherein the physiological parameter is the minute volume and the control function is linear, wherein obtaining the first activity value further comprises averaging a first plurality of minute volume measures obtained over a corresponding plurality of breathing cycles, the first being selected from between 16 and 64, and providing the first function as a multiple on the order of 6 times the minimum activity value.

27. A pacemaker having a programmed minimum pacing rate (FC low) and a programmed maximum pacing rate (FC max), comprising:
   a sensor for monitoring a physiological parameter (X) indicative of patient activity;
   means for providing a linear control relation for providing a selected pacing rate in response to a measure of the physiological parameter having as coefficients FC low and FC max;
   first means for calculating automatically a value X low and a value X max in response to an obtained measure of the physiological parameter corresponding to patient minimum and maximum activity levels, respectively, said first means recalculating automatically the values X low and X max in response to a second obtained measure of the physiological parameter; and
   means for adjusting the linear control relation to intersect two pairs of values (FC low, X low) and (FC max, X max) to correspond to the real needs of the patient.

28. The pacemaker of claim 27 wherein the physiological parameter (X) is the minute volume (VE) measured over a breathing cycle and the first calculating means further comprises means for receiving an initial minimum parameter VE low based on a mean minute volume value taken over a plurality of breathing cycles of the patient at rest, the plurality being selected from between 4 and 16, and means for determining an initial maximum parameter VE max to be equal to a number times the initial VE low, the number being selected from between 5 and 7, the first calculating means thereafter calculating the minimum and maximum values of VE low and VE max based on subsequently obtained measures of minute volume.

29. The apparatus of claim 28 further comprising means for recalculating the control relation after each modification of VE max as soon as the heart rate of the patient is less than a threshold rate defined as close to the rate FC low.

30. The pacemaker of claim 28 wherein the first calculating means further comprises a second means for calculating every M/2 breathing cycles a mean value VE/M of the measures of VE during M preceding cycles, M being selected from between 32 and 128, and means for comparing the mean value VE/M to an upper limit calculated as VE low + x% and to a lower limit VE low − x%, wherein x is selected from between 3 and 9; means for reducing VE low by x% if VE/M is less than the lower limit, and means for increasing VE low by x% if VE/M is greater than the upper limit for more than a selected number of overshootings of the upper limit and VE low is not modified during those overshootings, the selected number being between 4 and 12.

31. The pacemaker of claim 28 wherein the first means for calculating further comprises a second means for calculating the minute volume VE at each breathing cycle; a third means for calculating a mean value VE/N of the VE measures for the last N breathing cycles, N being selected from between 4 and 16; means for comparing the mean VE/N to the value of VE max; means for modifying VE max if VE/N is higher than VE max so that VE max, will be equal to the smallest of the value of VE/N and Z(VE max), wherein Z is selected from between 1.03 and 1.12; and first means for maintaining VE max the same if VE/N is less than VE max.

32. The pacemaker of claim 31 wherein the first calculating means further comprises means for lowering the value of VE max on the order of 3% to 6% if the value of VE max has not been modified during a selected period on the order of 12 to 48 hours.

33. The pacemaker of claim 32 wherein the lowering means and the modifying means further comprise a second means for maintaining the modified value of VE max between an upper limit corresponding to a theoretical maximum value of the ventilation MVV calculated as a second number times VE low, the second number being greater than 10, and a lower limit corresponding to a minimum value calculated as Y(VE low), Y being selected from between 2 and 5.

34. A method for controlling a pacemaker having a control relation between the pacing rate (FC) and a monitored minute volume (VE) of a patient, the control relation having coefficients defining the control relation of the pacing rate having a programmed minimum rate (FC low) and a programmed maximum rate (FC max), characterized by:
   defining a linear control relation a(VE)+b;
   initializing the control relation by calculating a minimum parameter VE low to be the mean value taken over a plurality of breathing cycles of the patient at rest, the plurality being selected from between 4 and 16, and providing a maximum parameter VE max;
   calculating automatically thereafter a value VE low and a value VE max corresponding to a minimum activity and a maximum activity in response to measures of the minute volume; and
   maintaining the control relation as a line intersecting two pairs of values (FC low, VE low) and (FC max, VE max) to correspond to the real needs of the patient.

35. A method according to claim 34, further characterized by calculating the minute volume VE at each breathing cycle, calculating a mean value VE/N of the VE measures for the last N breathing cycles, N being selected from between 4 and 16, comparing the mean VE/N to the value of VE max, modifying VE max if VE/N is higher than VE max so that VE max will be equal to the smallest of the value of VE/N and Z(VE max), wherein Z is selected from between 1.03 and 1.12, and maintaining VE max the same if VE/N is less than VE max.

36. A method according to claim 35, further characterized by lowering the value of VE max on the order of 3% to 6% if the value of VE max has not been modified during a selected period on the order of 12 to 48 hours.

37. A method according to claim 35, further characterized by maintaining the modified value of VE max between an upper limit corresponding to a theoretical maximum value of the ventilation MVV calculated as a second number times VE low, the second number being greater than 10, and a lower limit corresponding to a minimum value calculated as Y(VE low), Y being selected from among the group consisting of 2, 3, 4, or 5.

38. A method according to claim 34, further characterized by recalculating the control relation after each modification of VE max as soon as the heart rate of the patient is less than a threshold rate defined as close to the rate FC low.

39. A method according to claim 34, further characterized by calculating every M/2 breathing cycles a mean value VE/M of the measures of VE during M preceding cycles, M being selected from between 32 and 128, and comparing the mean value VE/M to an upper limit calculated as VE low+x% and to a lower limit VE low−x%, wherein x is selected from between 3 and 9; reducing VE low by x% if VE/M is less than the lower limit, and increasing VE low by x% if VE/M is greater than the upper limit for more than a selected number of overshootings of the upper limit and VE low is not modified during those overshootings, the selected number being between 4 and 12.

40. A method according to claim 34, further characterized by calculating a limit value VE low/max as being equal to VE low/mean+y%, wherein VE low/mean is equal to the mean value of 256 values of VE low calculated every 96 breathing cycles, y being selected from between 10 and 30.

41. In a pacemaker having a cardiac pacing rate that varies between a selected maximum rate and a selected minimum rate in response to a control function relating a monitored physiological parameter indicative of patient activity to a pacing rate, a method for adjusting the control function comprising:
(a) providing a minimum activity value for the physiological parameter corresponding to patient activity;
(b) providing a maximum activity value;
(c) calibrating the control function so that the provided minimum activity value relates to the selected minimum pacing rate and the provided maximum activity value relates to the selected maximum pacing rate;
(d) selecting the pacing rate in response to a measure of the physiological parameter using the calibrated control function;
(e) obtaining a first activity value based on a first time measure of the physiological parameter corresponding to the patient's average activity over a first time period;
(f) adjusting the maximum activity value in response to the first activity value being greater than the maximum activity value, so that the adjusted maximum activity value is the lesser of the first activity value and the preexisting maximum activity value times a first constant, the first constant being selected from between 1.03 and 1.12; and
(g) maintaining the maximum activity value unadjusted if it is greater than the first activity value.

42. The method of claim 41 further comprising:
(h) recalibrating the control function in response to the adjusted maximum activity value and the pacing rate decreasing below a selected rate threshold; and thereafter
(i) selecting the pacing rate in response to a measure of the physiological parameter using the recalibrated control function.

43. The method of claim 42 wherein step (f) further comprises adjusting the maximum activity value in response to the maximum activity value not being adjusted during a third time period, the third time period being greater than the second time period, so that the adjusted value is the preexisting maximum activity value times a second constant selected from between 0.93 and 0.97.

44. The method of claim 43 wherein step (f) further comprising:
providing an upper limit for the value of the maximum activity value as a second function of the minimum activity value;
providing a lower limit for the value of the maximum activity value as a third function of the minimum activity value; and
limiting the value of the maximum activity value to between the upper and lower limits.

45. The method of claim 44 wherein the second function is n times the minimum activity value, where n is selected to be greater than 10 and the third function is m times the minimum activity level, where m is selected from between 2 and 5.

46. The method of claim 44 further comprising;
(j) obtaining a second activity value based on a second time measure of the physiological parameter corresponding to the patient's average activity over a second time period;
(k) adjusting the minimum activity value in response to the second activity value being less than the minimum activity value by more than a first percent, the first percent being selected from between 3 and 9 percent, so that the adjusted value of the minimum activity level is the preceding value reduced by the selected percent; and
(l) adjusting the minimum activity value in response to the second activity value being greater than the minimum activity value by more than a second selected percent for longer than a fourth period of time during which the minimum activity value is not adjusted, so that the adjusted value of the minimum activity value is the preceding value increased by the second percent, the second percent being selected from between 3 and 9 percent.

47. The method of claim 46 wherein step (k) further comprises:
calculating an average of the minimum activity value values over a fifth period of time; and
providing an upper limit for the minimum activity value as a fourth function of the calculated average minimum activity level.

48. The method of claim 47 wherein the fourth function is l times the calculated average minimum activity level, l being selected from between 1.1 and 1.3.

49. The method of claim 46 wherein the physiological parameter is the minute volume and the control function is linear, wherein obtaining the first activity value further comprises averaging the minute volume measures obtained over the last N number of breathing cycles N being selected from between 4 and 16, the third time period being selected from between 12 and 48 hours, and wherein providing the second activity value further comprises calculating every M number of breathing cycles a mean value of the preceding minimum activity values during a T number of preceding breathing cycles, wherein M is selected from between 16 and 64 and T is selected from between 34 and 128.

50. The method of claim 41 wherein step (a) further comprises obtaining a first activity value based on a first time measure of the physiological parameter corresponding to the patient being in a rest activity level and, setting the minimum activity value to be the first activity value.

51. The method of claim 50 wherein the physiological parameter is the minute volume and the control function is linear, wherein obtaining the first activity value further comprises averaging a first plurality of minute volume measures obtained over a corresponding plurality of breathing cycles, the first being selected from between 16 and 64, and providing the maximum activity value for initializing further comprises calculating the maximum activity value as a multiple on the order of 6 times the minimum activity value.

52. A method of claim 41 wherein the physiological parameter is the minute volume and the control function is linear, providing the maximum activity value for initializing further comprises calculating the maximum activity value as a multiple on the order of 6 times the minimum activity level, wherein obtaining the first activity value further comprises averaging the minute volume measures obtained over the N most recent breathing cycles wherein N is selected from between 4 and 16.

53. The method of claim 41 further comprising:
modifying the maximum activity value in response to the trend of a first measure of the physiological parameter representative of maximum activity levels differing from the existing maximum activity value by more than a first threshold amount; and
recalibrating the control function using the modified value maximum activity.

54. The method of claim 53 further comprising:
modifying the minimum activity value in response to the trend of a second measure of the physiological parameter representative of minimum activity levels differing from the existing minimum activity value by more than a second threshold amount; and
recalibrating the control function using the modified maximum activity value.

55. In a pacemaker having a control relation between the pacing rate (FC) and a monitored minute volume physiological parameter (VE) measured over a breathing cycle of the patient indicative of patient activity, the control relation having coefficients defining a programmed minimum rate (FC low) and a programmed maximum rate (FC max), apparatus for adjusting a control relation, comprising:
means for receiving an initial minimum parameter VE low based on a mean minute volume value taken over a plurality of breathing cycles of the patient at rest, the plurality being selected from between 4 and 16;
means for receiving an initial maximum parameter VE max;
first means for calculating automatically a value VE low and a value VE max in response to subsequently obtained measures of the minute volume corresponding to patient maximum and minimum activity levels, respectively; and
means for adjusting the control relation to intersect two pairs of values (FC low, VE low) and (FC max, VE max) to correspond to the real needs of the patient.

56. The apparatus of claim 55 wherein the first means for calculating further comprises a second means for calculating the minute volume VE at each breathing cycle; a third means for calculating a mean value VE/N of the VE measures for the last N breathing cycles, N being selected from between 4 and 16; means for comparing the mean VE/N to the value of VE max; means for modifying VE max if VE/N is higher than VE max so that VE max, will be equal to the smallest of the value of VE/N and Z(VE max), wherein Z is selected from between 1.03 and 1.12; and first means for maintaining VE max the same if VE/N is less than VE max.

57. The apparatus of claim 56 wherein the first calculating means further comprises means for lowering the value of VE max on the order of 3% to 6% if the value of VE max has not been modified during a selected period on the order of 12 to 48 hours.

58. The apparatus of claim 57 wherein the lowering means and the modifying means further comprise a second means for maintaining the modified value of VE max between an upper limit corresponding to a theoretical maximum value of the ventilation MVV calculated as a second number times VE low, the second number being greater than 10, and a lower limit corresponding to a minimum value calculated as Y(VE low), Y being selected from between 2 and 5.

59. The apparatus of claim 55 further comprising means for recalculating the control relation after each modification of VE max as soon as the heart rate of the patient is less than a threshold rate defined as close to the rate FC low.

60. The apparatus of claim 55 wherein the first calculating means further comprises a second means for calculating every M/2 breathing cycles a mean value VE/M of the measures of VE during M preceding cycles, M being selected from between 32 and 128, and means for comparing the mean value VE/M to an upper limit calculated as VE low+x% and to a lower limit VE low−x%, wherein x is selected from between 3 and 9; means for reducing VE low by x% if VE/M is less than the lower limit, and means for increasing VE low by x% if VE/M is greater than the upper limit for more than a selected number of overshootings of the upper limit and VE low is not modified during those overshootings, the selected number being between 4 and 12.

* * * * *

UNITED STATES PATENT AND TRADEMARK OFFICE
CERTIFICATE OF CORRECTION

PATENT NO. : 5,303,702
DATED : April 19, 1994
INVENTOR(S) : Bonnet et al.

It is certified that error appears in the above-indentified patent and that said Letters Patent is hereby corrected as shown below:

Column 14, lines 29-30 "i=0" should be moved to after "-2+i modulo 4))/2";

Column 16, lines 21-22, after ""Min vent calib"" insert as a new line --"Counter aver" = "Counter aver" + 1--;

Column 20, line 11, between "calib + 1<" and "vent + 1" should be --max volunt--;

Column 24, line 40, after "cali" insert --aver--;

Column 26, line 24, after "vent + ", delete "." and insert --1 < max--;

Column 29, line 19, "A" should be --The--;

UNITED STATES PATENT AND TRADEMARK OFFICE
CERTIFICATE OF CORRECTION

PATENT NO. : 5,303,702
DATED : April 19, 1994
INVENTOR(S) : Bonnet et al.

It is certified that error appears in the above-indentified patent and that said Letters Patent is hereby corrected as shown below:

Column 29, line 53, "comprising" should be --comprises--;

Column 31, line 44, "apparatus" should be to --pacemaker--;

Column 34, line 2, "comprising" should be --comprises--.

Signed and Sealed this

Twenty-ninth Day of November, 1994

Attest:

BRUCE LEHMAN

*Attesting Officer*    *Commissioner of Patents and Trademarks*